United States Patent [19]

Bentzen et al.

[11] Patent Number: 4,696,920
[45] Date of Patent: Sep. 29, 1987

[54] CERTAIN 2-SUBSTITUTED 1,3-PROPYLIDENEDIPHOSPHONATE DERIVATIVES, PHARMACEUTICAL COMPOSITIONS CONTAINING THEM AND THEIR USE AS ANTIHYPERTENSIVE AGENTS

[75] Inventors: Craig L. Bentzen, Chavannes-de-bogis, Switzerland; Yves Guyon-Gellin, Annemasse, France; Kyriacos Kalathakis, Grand-Lancy, Switzerland; Hieu T. Phan, Tannay, Switzerland; Lân Nguyen Mong, Nyon, Switzerland; Eric Niesor, Gland, Switzerland; Jean-Robert Rossier, Grand-Lancy, Switzerland

[73] Assignee: Symphar S.A., Le Lignon, Switzerland

[21] Appl. No.: 755,712

[22] Filed: Jul. 16, 1985

[30] Foreign Application Priority Data

Jul. 18, 1984 [CH] Switzerland .......................... 3488/84

[51] Int. Cl.$^4$ .......................... C07F 9/58; C07F 9/40; A61K 31/675; A61K 31/66
[52] U.S. Cl. ....................................... 514/89; 514/100; 514/102; 514/107; 546/22; 260/502.4 P; 549/220; 558/161; 558/162; 558/163
[58] Field of Search .................. 546/22; 558/161, 162, 558/163; 260/502.4 P; 549/220; 514/89, 100, 102, 107

[56] References Cited

U.S. PATENT DOCUMENTS

| 3,256,370 | 6/1966 | Fitch et al. | 260/502.4 P |
| 3,420,917 | 1/1969 | Wu | 558/161 |
| 4,309,364 | 1/1982 | Bentzen et al. | 558/163 |
| 4,371,527 | 2/1983 | Bentzen et al. | 514/107 |
| 4,416,877 | 11/1983 | Bentzen et al. | 514/107 |

FOREIGN PATENT DOCUMENTS

| 0023173 | 1/1981 | European Pat. Off. | 260/502.4 P |
| 2351126 | 12/1977 | France | 260/502.4 P |

Primary Examiner—Alan L. Rotman
Attorney, Agent, or Firm—Young & Thompson

[57] ABSTRACT

2-Substituted-1,3-propylidenediphosphonates of formula (I), where A, $R^1$ and $R^2$ are defined in claim 1, are therapeutically active compounds, namely for the treatment of cardiovascular diseases.

They can be prepared by reacting phosphonating agents with 1,3- dibromopropanes or ditosylates of 1,3-propanediols substituted in position 2.

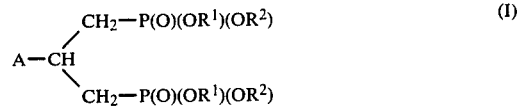

29 Claims, No Drawings

CERTAIN 2-SUBSTITUTED 1,3-PROPYLIDENEDIPHOSPHONATE DERIVATIVES, PHARMACEUTICAL COMPOSITIONS CONTAINING THEM AND THEIR USE AS ANTIHYPERTENSIVE AGENTS

This invention relates to a novel class of compounds, 1,3-propylidene diphosphonate derivatives substituted at position 2, as well as the process for preparing such compounds. It further relates to pharmaceutical compositions containing said compounds for the treatment of cardiovascular diseases such as angina pectoris, arrhythmia and hypertension.

The Japanese Pat. No. 8 098 193 of Nissan Chemical Industries discloses the preparation of several (pyridylmethyl)-1,1-methylenediphosphonate compounds useful as herbicidal agents.

The UK Pat. No. 2 079 285 of Symphar SA reports the preparation of several phenylalkyl-1,1-methylenediphosphonates and their use as antiatherosclerotic agents.

The compounds disclosed in the two previous references are geminal diphosphonate derivatives, i.e. products wherein the two phosphonate groups are bound to the same carbon. These compounds are prepared according to the following reaction:

$$A-X + CH_2(PO_3R_2)_2 \rightarrow A-CH(PO_3R_2)_2$$

A = pyridylmethyl (Nissan Chemical Patent) or phenylalkyl (Symphar Patent)

The above process for preparing 1,1-methylenediphosphonates is clearly distinct from the novel process described in this application (see synthetic scheme p. 11) for the synthesis of 1,3-propylidenediphosphonates.

The German Pat. No. 2 535 685 of Bayer AG discloses a process for the synthesis of several known 1,3-propylidene diphosphonates and 2-methyl-1,3-propylidene diphosphonates by reacting respectively allyl and methallylphosphonates with dialkyl phosphite in the presence of a radical-initiating agent.

$$CH_2=C(A)-CH_2-PO_3R_2 + HP(O)(OR)_2 \rightarrow R_2O_3P-CH_2-CH(A)-CH_2-PO_3R_2$$

A = H and Me

These compounds are useful as corrosion inhibitors and sequestering agents. The scope of this process is however limited due to the scarce availability of the starting materials: allylphosphonate derivatives. It should also be noted that the compounds described in the Bayer patent are known products: the synthesis of tetraethyl 1,3-propylidenediphosphonate has previously been reported in Houben Weyl, Methoden der Organischen Chemie XII, 1, p. 438, Georg Thieme Verlag, Stuttgart, 1964.

The foregoing survey of the prior-art literature shows that 2-substituted-1,3-propylidenediphosphonate derivatives (I) disclosed in this application form a novel class of products, excepted for the first two members of the series (A=H and Me).

This class of products has been discovered to have profound and unexpected effects upon muscular activity by acting as calcium regulating agents. These compounds are potent vasoactive agents and therefore have a therapeutic potential for the treatment of various cardiovascular disease states such as angina pectoris and hypertension.

The present invention relates to compounds of formula (I)

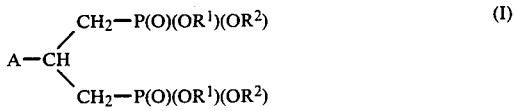

where $R^1$ and $R^2$, identical or different, are H, metal ions such as sodium, potassium, magnesium, ammonium, substituted ammonium groups, alkyl groups from 1 to 8 carbon atoms, alkenyl or alkynyl groups from 2 to 8 carbon atoms, or cyclopentyl, cyclopentylmethyl, cyclohexyl, cyclohexylmethyl, phenyl, benzyl, $CH_2CH_2OCH_3$, $CH_2CH_2OCH_2CH_3$, $CH_2CH_2OH$, $CH_2CH_2NMe_2$, and A is selected from the group comprising

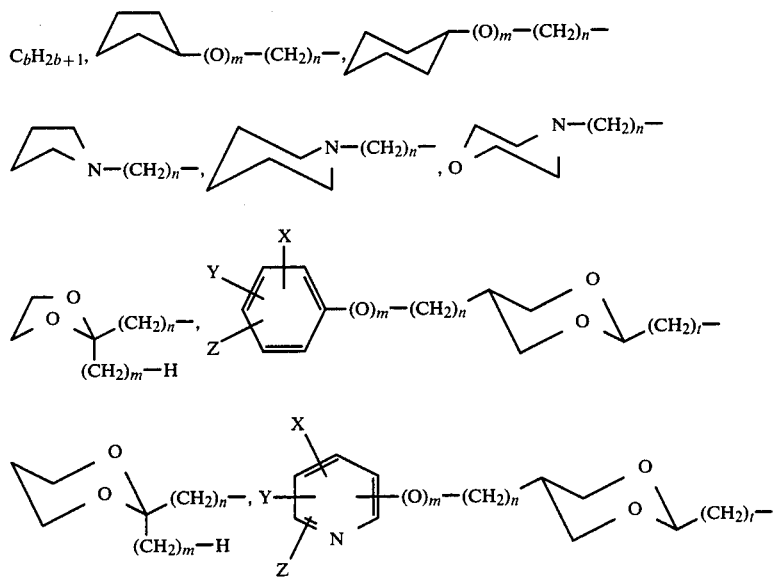

-continued

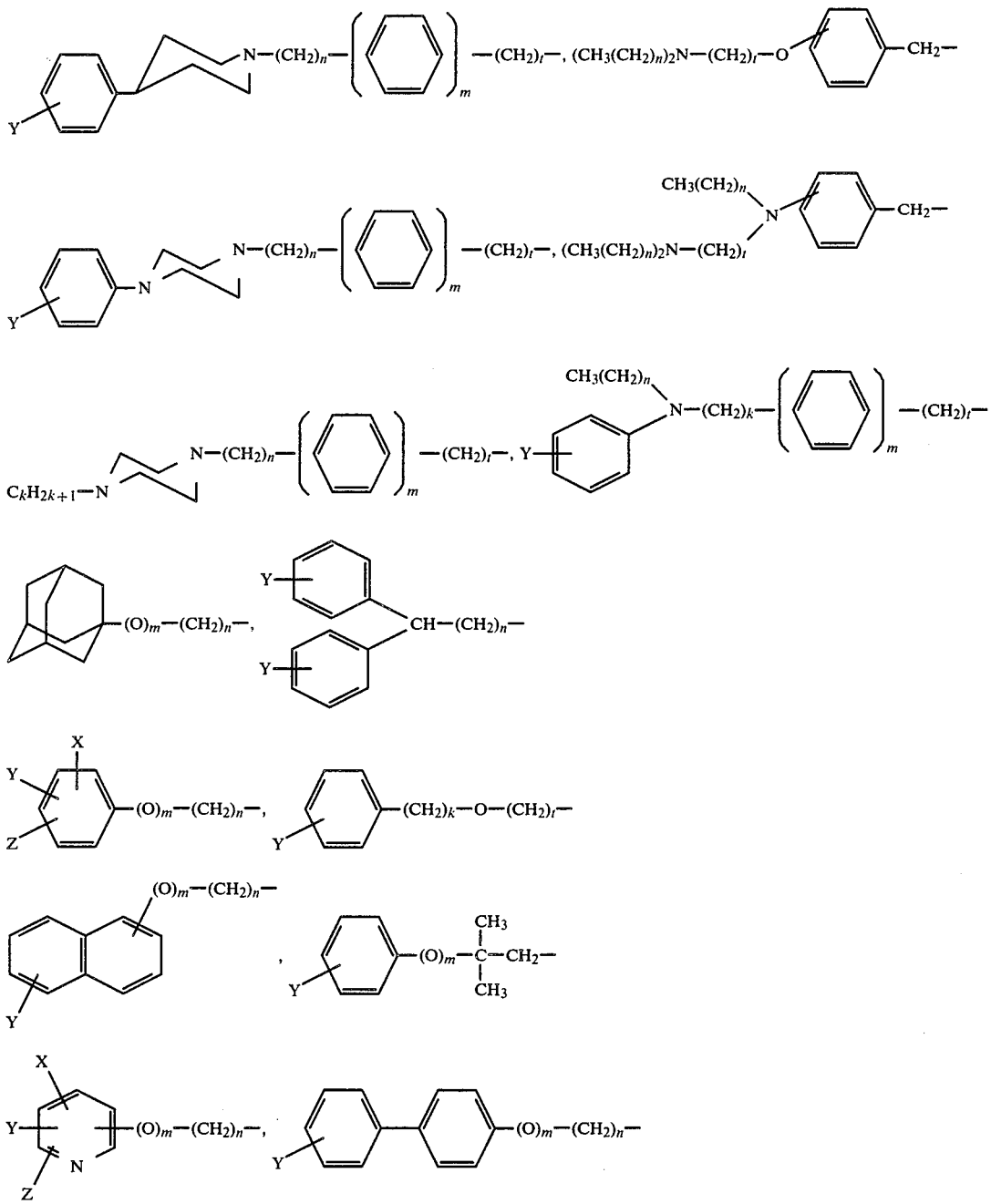

where b is an integer from 3 to 16, m is zero or 1, n is an integer from zero to 8, k is an integer from zero to 4, t is an integer from 1 to 4, X, Y and Z identical or different are an atom or a group such as H, F, Cl, Br, I, $CF_3$, $CHF_2$, $NO_2$, CN, $CH_3$, $C_2H_5$, $CH_2=CH-CH_2$, normal-$C_3H_7$, iso-$C_3H_7$, normal-$C_4H_9$, iso-$C_4H_9$, OH, $CH_2OH$, $-O-CH_2-O-$, $OCH_3$, $OC_2H_5$, $OC_3H_7$, $OC_4H_9$, $SCH_3$, $NH_2$, $NMe_2$, $NEt_2$, $(CH_2)_t-NMe_2$, $(CH_2)_t-NEt_2$ where t is described as above.

The invention also relates to a process for the preparation of compounds of formula (I) which comprises reacting phosphonating agents (trialkyl phosphite or dialkyl phosphite, respectively of formula $P(OR^1)(OR^2)_2$ and $HP(O)(OR^1)(OR^2)$ with 2-substituted 1,3-dibromopropanes (compound V, Z=Br) or ditosylate of 2-substituted-1,3-propanediols (V, Z=OTs).

The invention finally relates to pharmaceutical compositions comprising at least one compound of formula (I) for the treatment of diseases where defects in calcium regulatory activities are implicated, namely heart diseases, angina pectoris, arrythmia and hypertension.

It is to be understood that, for convenience of notation, all of the compounds falling within the above formula (I) are generically described in this application as 1,3-diphosphonates. In other words, the acids, salts, esters and mixtures thereof are all generically described herein as 1,3-diphosphonates.

1,3-Diphosphonate compounds of formula (I) where $R^1$, $R^2$ and A are defined as above can be prepared according to the general reaction sequence represented on page 11.

Substituted malonates (III) are obtained by reacting appropriate halides (II) with diethyl malonate in presence of a base. Reduction with lithium aluminium hydride affords 2-substituted-1,3-propanediols (IV) which are converted into the corresponding 1,3-dibromopropanes (V, Z=Br) or ditosylates of 1,3-propanediols (V, Z=OTs) by following standard procedures.

In the final step, 2-substituted-1,3-propylidenediphosphonates (I) are prepared by either of two general methods described below.

The first method consists in heating the 2-substituted-1,3-dibromopropane (V, Z=Br) with an excess of trialkyl phosphite at a temperature between 110° and 200° C. At this temperature the formed alkyl bromide $R^2$-Br is distilled off, leaving behind the 1,3-diphosphonate (I) that is purified by distillation.

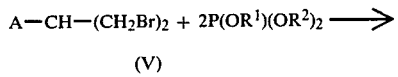

(V)

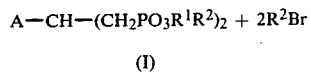

(I)

In the second method, 1,3-diphosphonates (I) are prepared by treating the 1,3-dibromides (V, Z=Br) or 1,3-ditosylates (V, Z=OTs) with dialkyl phosphite under alkaline conditions. The experimental procedure consists in first reacting dialkyl phosphite with an alkali base, preferably sodium hydride, in tetrahydrofuran. A solution of compound V (Z=Br or OTs) dissolved in 1,4-dioxane is then added to the prepared solution of sodium dialkyl phosphite and the resulting mixture is heated to reflux.

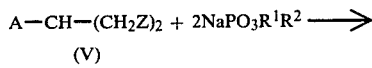

(V)

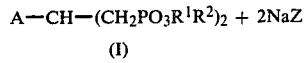

(I)

Z=Br or OTs

The advantage of the second process consists in that the sodium bromide or sodium tosylate formed gradually precipitates out, leaving in solution the 1,3-diphosphonate that is easily purified by distillation under reduced pressure.

The afore-mentioned experimental conditions: sodium hydride and a 1:1 mixture of tetrahydrofuran and dioxane are representative examples of the second phosphonation method. Other suitable conditions include using as a base sodium or potassium metal and as diluent media anhydrous aprotic solvents, e.g. hydrocarbons such as hexane, heptane, benzene or toluene or ethers such as dimethoxyethane. These solvents can be utilized pure (dimethoxyethane, toluene) or as a mixture (heptane/tetrahydrofuran, toluene/dioxane). The phosphonation reaction is generally conveniently conducted at reflux temperature of the pure solvent or mixture of solvents.

A great variety of trialkylphosphites and dialkyl phosphites ($R^1=R^2$) used in above described methods are either commercially available or easily accessible by standard synthetic procedures (H. McCombie et al J. Chem. Soc., 1945, 380). Mixed trialkyl phosphites and mixed dialkylphosphites ($R^1 \neq R^2$) are prepared by stepwise reactions between $PCl_3$ and corresponding alcohols according to Houben Weyl, Methoden der organischen Chemie XII, 2, p. 26 and 62, Georg Thieme Verlag, Stuttgart, 1964.

Tetraalkyl 1,3-diphosphonates can be partially hydrolyzed with an alkaline solution or sodium iodide in acetone to yield bis (alkyl, hydrogen) 1,3-diphosphonates of formula (I), ($R^1$=alkyl, $R^2$=H).

Mixed tetraalkyl 1,3-diphosphonates of formula (I) ($R^1 \neq R^2$), in addition to being prepared by the standard procedure: mixed dialkylphosphites/base or mixed trialkyl phosphites, can also be synthesized by esterification of bis (alkyl, hydrogen)-1,3-diphosphonates with diazoalkanes or trialkyl orthoformate having the appropriate alkyl groups.

Functional groups that may reveal unstable in the reaction conditions of the general procedure can be kept intact by slight modifications of the synthetic sequence. Groups such as CN or $NO_2$ are introduced after the phosphonation procedure: e.g. CN by reacting the corresponding bromo-phenyl derivative with copper (I) cyanide in dimethyl formamide, $NO_2$ by nitration of the phenyl ring using standard procedures (see example 20). Other functional groups, such as OH, $CH_2OH$ are protected as substituted methyl ethers such as methoxymethyl ether (MOM ether), 2-methoxyethoxy methyl ether (MEM ether), benzyl ether or as a ketal such as isopropylidene ketal. Subsequent to the phosphonation step, these protective groups are removed by mild cleavage conditions such as dilute aqueous solutions for MOM, MEM ethers or isopropylidene ketals and catalytic hydrogenation over Pd for benzyl ethers. Example 21 is provided to illustrate the simultaneous protection of OH and $CH_2OH$ groups.

It is to be appreciated that 2-substituted-1,3-propanediol of formula (IV) can be converted to ω-bromoalkyl cyclic acetals by following the procedures described in Journal of Pharmaceutical Sciences 60, p. 1250 (1971) and references cited therein.

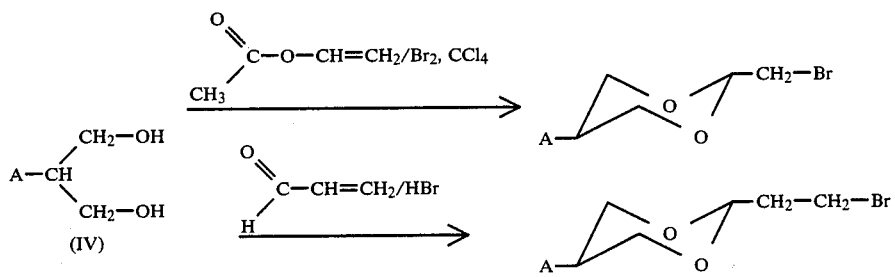

These ω-bromocyclic acetals can be used as starting compounds for the synthesis of 2-(cyclic acetal)-1,3-propylidenediphosphonates by following the general synthetic scheme described in this application. Examples 23 and 24 are provided to illustrate the preparation of such derivatives.

The particular instances of 1,3-propylidenediphosphonate compounds of formula (I) where $R^1$ and $R^2$ are H, $CH_3$ or $CH_2CH_2-NMe_2$ are synthesized according to the additional steps described below.

1,3-Diphosphonic acids (I, $R^1$ 32 $R^2$ = H) are prepared by hydrolysis of tetraethyl 1,3-diphosphonates (I, $R^1 = R^2 = C_2H_5$) with hydrochloric acid or bromotrimethylsilane and water.

Tetramethyl 1,3-diphosphonates (I, $R^1 = R^2 = CH_3$) are obtained by reacting 1,3-diphosphonic acids with trimethyl orthoformate.

Reaction of tetraethyl 1,3-diphosphonates with bromotrimethylsilane followed by treatment with phosphorus pentachloride affords 1,3-diphosphonyl tetrachloride. These compounds are then reacted with 2-(dimethylamino)ethanol to yield tetrakis (2-dimethylamino ethyl) 1,3-diphosphonates (I, $R^1 = R^2 = CH_2CH_2NMe_2$).

The process for preparing 2-substituted-1,3-propylidenediphosphonates (I) will be further illustrated by examples 1 to 24 described in the following pages.

distilled is placed in the ball at the far end of the oven and vacuum is applied to the whole system. The oven temperature is slowly raised to attain a value slightly higher (5°-10° C.) than the boiling point of the compound. As vapors of the distillate travel only a very short distance before being condensed in the next ball, the distillation can be carried out at the lowest temperature possible, therefore minimizing the extent of thermal decomposition.

Boiling point values listed in table I are oven temperatures noted for each ball-tube distillation.

The structures of compounds of formula (I) were established by the mode of synthesis, by elemental analysis and by infrared (IR), mass (MS) and nuclear magnetic resonance (NMR) spectroscopic determinations. The purity of the compounds was verified by silicagel thin layer chromatography (general conditions of elution: a $CHCl_3/CH_3OH$ mixture from 95/5 to 80/20 (v/v)) and gas liquid chromatography (3% Silar column, 150 cm × mm id., general conditions of chromatography: 120° (2 min hold), 4°/min until from 200° to 300° (30 min hold).

All compounds of formula (I) display IR absorption bands pertaining to the phosphonate functional groups: 1240 cm$^{-1}$ (P=O) and 1070-990 cm$^{-1}$ (P—O—C—).

NMR spectra of 2-substituted-1,3-propylidenediphosphonates (I) also present a characteristic pattern:

SYNTHETIC SCHEME

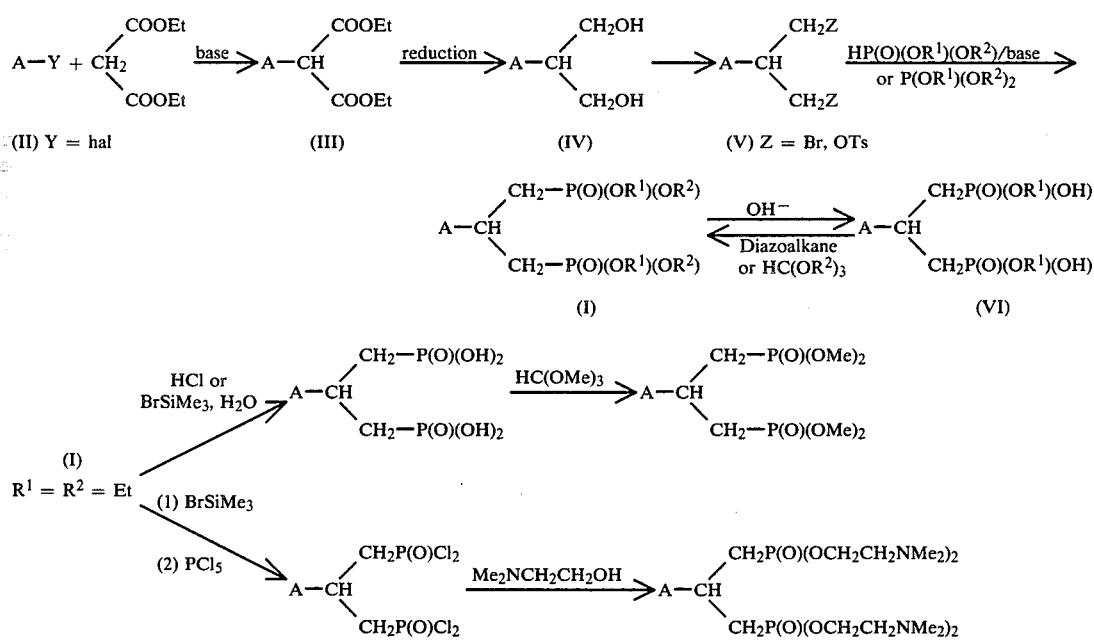

2-Substituted 1,3-propylidenediphosphonates (I) are in general high boiling oils that are purified by distillation at reduced pressure. These distillations are most conveniently and efficiently carried out in a ball tube distillation apparatus commonly referred to as "Kugelrohr". The description of such an apparatus has been published by A. W. Schrecker, Analytical Chemistry 29, p. 113–114 (1957) "Bulb Tube Assembly for Vacuum Disillation".

The apparatus consists essentially of a transparent glass oven and several assembled ground-joint balls that are rotated at a constant speed. The compound to be

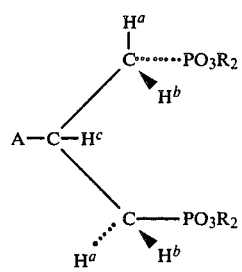

The geminal methylene protons $H^a$ and $H^b$ are diastereotopic nuclei and absorb at two different chemical shifts: $\delta=2.3-2.0$ and $\delta=2.10-1.8$. The lower field absorption is a doublet of doublet of doublet (dxdxd) with three coupling constants: $J_{Ha-Hc}=7$ Hz, $J_{Ha-Hb}$(geminal coupling)=16 Hz, and $J_{H-P}=19-20$ Hz. In the higher field absorption, the similar multiplet (dxdxd) is further split by long range couplings with the second phosphorus atom. The methine proton $H^c$ absorbs as a large multiplet in the vicinity of $\delta=2.5$.

The present invention will be further described by reference to the following examples 1 through 24 directed to the preparation of representative compounds of formula (I).

EXAMPLE 1

Tetraethyl 2-benzyl-1,3-propylidenediphosphonate

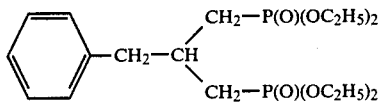

A solution of diethyl benzylmalonate (107 g, 0.43 mol) in 300 ml dry diethyl ether was added under nitrogen to a suspension of 24.5 g (0.65 mol) lithium aluminium hudride (LiAlH₄) in 220 ml dry ether so to maintain a gentle reflux. The reaction mixture was refluxed for 2 more hours after the addition was completed. The excess of LiAlH₄ was destroyed by addition of 50 ml ethyl acetate, followed by 50 ml water and finally by 600 ml 15% sulfuric acid. The ether phase was extracted by a saturated sodium bicarbonate solution and a saturated sodium chloride solution and dried over magnesium sulfate. Evaporation of the solvent left a white solid that was purified by recrystallization in ether. An amount of 45.8 g (0.28 mol) of 2-benzyl-1,3-propanediol was obtained (yield=64%).

mp=65°-67°

IR (KBr): 3300 cm⁻¹ (OH), 1450 (OH) and 1030 (C—O)

To a solution containing 114 g (0.6 mol) p-toluenesulfonyl chloride (tosyl chloride) in 200 ml dry pyridine cooled to 0° there was added a solution of 45 g (0.27 mol) 2-benzyl-1,3-propanediol in 40 ml dry pyridine. The progression of the reaction could be followed by observing the separation of white needles of pyridine hydrochloride. The mixture was stirred at 0° for 2 hours and then at room temperature overnight. The reaction mixture was cooled to −25° for 2 hours and then poured on 500 ml ice-water. The white solid that separated out was collected by filtration and purified by recrystallization in acetone. There were obtained 104 g (0.22 mol) of ditosylate of 2-benzyl-1,3-propanediol (80% yield).

mp=88°-90°

IR (KBr)=1360 and 1170 cm⁻¹: (—SO₂—)

A 3.5 Molar solution of sodium diethyl phosphite was then prepared in the following manner:

A 9.0 g amount of a 80% dispersion of sodium hydride in mineral oil (0.30 mol) was suspended in 15 ml tetrahydrofuran. After stirring for 5 min the solid was allowed to settle and the supernatant was removed by pipet. Then sodium hydride was resuspended in 30 ml dry tetrahydrofuran and 45 g (0.33 mol) diethyl phosphite were added dropwise. Vigorous evolution of hydrogen was observed, accompanied by the progressive consumption of sodium hydride. The mixture was stirred at room temperature for an additional hour and then diluted to a total volume of 85 ml tetrahydrofuran. In this way completely clear solution was obtained that contained ca 3.5 mol/l sodium diethyl phosphite.

To the above solution of sodium diethyl phosphite there was added dropwise a solution of 33 g (0.07 mol) ditosylate of 2-benzyl-1,3-propanediol dissolved in 85 ml 1,4-dioxane. A voluminous white precipitate of sodium tosylate separated out soon after the reaction mixture was heated to reflux at approximately 80° C. After 4 hours of reflux the reaction mixture was concentrated under vacuum and partitioned between 50 ml water and 300 ml chloroform. The chloroform phase was dried over MgSO₄ and evaporated leaving a pale yellow oil. Volatile materials were removed by heating the crude mixture up to 150° under a 0.05 mm Hg vacuum. The residue was then purified by short-path distillation in a ball tube distillation apparatus. An amount of 21 g (52 mmol) tetraethyl 2-benzyl-1,3-propylidenephosphonate was obtained as a colorless oil.

bp=153°-155° (0.05 mm Hg)

yield=74%

Elemental analysis C₁₈H₃₂O₆P₂: Theor: % C 53.20; % H 7.94; % P 15.24; Found: % C 53.49; % H 8.18; % P 15.00

IR (liquid film): 3050 cm⁻¹: aromatic C—H; 2990: aliphatic C—H; 1240: P=O; 1170: P—O—C₂H₅; 1030: P—O—C; 790: aromatic C—H NMR (CDCl₃) $\delta=7.30-7.15$ (multiplet, 5H): Aromatic H; 4.15-3.95 (multiplet, 8H): P—O—C$\underline{H}$₂CH₃; 2.90 (doublet, J=7 Hz, 2H): Ph—C$\underline{H}$₂; 2.58-2.40 (multiplet, 1H): Ph—CH₂—C$\underline{H}$; 2.04 (doublet of doublet of doublet, J=7, 16 and 19 Hz, 2H): diastereotopic $H^a$: —C($\underline{H}^a$)($H^b$)—PO₃Et₂; 1.83 (finely split doublet of doublet of doublet, 2H): diastereotopic $H^b$: —C($H^a$)($\underline{H}^b$)—PO₃Et₂; 1.28 and 1.30 (two triplets, J=7 Hz, 12H): P—O—CH₂—C$\underline{H}$₃

This compound can also be prepared by reacting 2-benzyl-1,3-dibromopropane with triethyl phosphite as described below.

Phosphorus tribromide (13.0 g, 48 mmol) was added to 2-benzyl-1,3-propanediol (8.0 g, 48 mmol) cooled to 0° and the reaction mixture was stirred for five days at room temperature. The viscous mass was heated at 100° for two hours and was poured on ice-water. Extraction with ether and vacuum distillation gave 7.8 g (56% yield) of 2-benzyl-1,3-dibromopropane.

bp=79°-83° (0.05 mm Hg)

MS: m/e=294 (M+4)⁺; 292 (M+2)⁺; 290 (M)⁺

A mixture of 5 g (17 mmol) of the above dibromide and 17 g (100 mmol) triethyl phosphite was refluxed at 160° for 20 hours. Removal of the excess of triethyl phosphite followed by ball-tube distillation gave 4.8 g (70% yield) of tetraethyl 2-benzyl-1,3-propylidenediphosphonate. This compound gave identical IR and NMR spectra and had the same retention time on GLC chromatography with the material obtained by reacting the ditosylate of 2-benzyl-1,3-propanediol with sodium diethyl phosphite as described above.

EXAMPLE 2

Tetraethyl 2-phenyl-1,3-propylidenediphosphonate

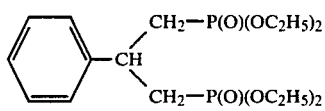

2-Phenyl-1,3-dibromopropane was prepared by reacting 2-phenyl 1,3-propanediol with phosphorus tribromide according to W. M. Schubert and S. M. Leahy, Journal of American Chemical Society 79, p. 381 (1957).

To a solution of sodium diethyl phosphite prepared by reacting 9.42 g (68 mmol) diethyl phosphite with 1.84 g (61 mmol) 80% dispersion sodium hydride in mineral oil in 17 ml tetrahydrofuran there was added a solution of 4 g (14.4 mmol) 2-phenyl-1,3-dibromopropane in 17 ml dioxane. Sodium bromide separated out when the reaction mixture was heated at 80° for two hours. The organic solvents were evaporated and the residue was partitioned between ether and water. Volatile materials were removed by heating the organic extracts up to 130° under a 0.05 mm Hg vacuum. Gas liquid chromatography analysis showed the high boiling residue to be a mixture of two products (GLC conditions: 3% Silar 2100 column, 150 cm×3 mm id, temperature program: 120° (2 min hold), 4°/min until 200° (30 min hold).

Separation of the two compounds was performed by column chromatography using silicagel as support and chloroform as eluent.

The first compound (1.0 g, 18% yield) to elute from the column was identified by IR and NMR spectroscopies as tetraethyl 1-methyl-1-phenyl-1,2-ethylenediphosphonate represented by the following formula:

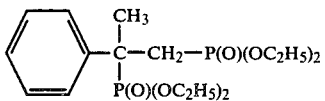

IR (liquid film): 3060 cm$^{-1}$: aromatic C—H; 2980: aliphatic C—H; 1240: P—O; 1165: P—O—Et; 1040: P—O—C; 790+690: aromatic C—H NMR (CDCl$_3$): δ=7.55-7.2 (multiplet, 5H); Aromatic H; 4.0, 3.85, 3.70 and 3.50 (four separate multiplets, 8H) P—O—C$\underline{H}_2$—CH$_3$; 2.93 (triplet of doublets, J=8, 17 and 25 Hz, 1H) diastereotopic H$^a$: —C($\underline{H}^a$)(H$^b$)—PO$_3$Et$_2$; 2.36 (finely split triplet of doublets, 1H): diastereotopic H$^b$: C—(H$^a$)($\underline{H}^b$)—PO$_3$Et$_2$; 1.85 (doublet, J=18 Hz, 6H): branched CH$_3$ group; 1.25, 1.10, 1.0 and 0.94 (four separate triplets, J=7 Hz, 12H): P—O—CH$_2$—C$\underline{H}_3$ The second product (1.3 g, 24% yield) was similarly identified by IR and NMR as the title compound, tetraethyl 2-phenyl-1,3-propylidenediphosphonate.

IR (liquid film): 3050 cm$^{-1}$: aromatic C—H; 2980: aliphatic C—H; 1240: P=O; 1165: P—O—Et; 1030: P—O—C; 780+690: aromatic C—H NMR (CDCl$_3$): δ=7.30-7.16 (multiplet, 5H): aromatic H; 3.95-3.76 (multiplet, 8H); P—O—CH$_2$—CH$_3$; 3.52-3.38 (multiplet, 1H); Ph—C$\underline{H}$; 2.43-2.30 (doublet of doublet of doublet, J=6, 16 and 19 Hz, 2H): diastereotopic H$^a$: —C($\underline{H}^a$)(H$^b$)—PO$_3$Et$_2$; 2.18-2.05 (doublet of doublet of doublet, J=9, 16 and 22 Hz, 2H): diastereotopic H$^b$: —C(H$^a$)($\underline{H}^b$)—PO$_3$Et$_2$; 1.15 and 1.16 (two triplets, J=7 Hz, 12H): P—O—CH$_2$—C$\underline{H}_3$.

EXAMPLE 3

2-Benzyl-1,3-propylidenediphosphonic acid

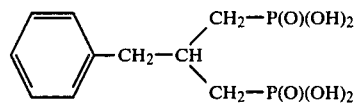

A mixture of 5 g (12.3 mmol) tetraethyl 2-benzyl-1,3-propylidene diphosphonate and 33 g of 37% hydrochloric acid was refluxed for 15 hours. Evaporation of the acid solution under vacuum left a white solid residue (3.6 g, 100% yield).

mp=158°-160°

IR (KBr)=2900+2300 cm$^{-1}$ (broad): PO—H; 1500: aromatic C—C; 1260+1110: P=O; 990+940: P—OH

EXAMPLE 4

Tetramethyl 2-benzyl-1,3-propylidenediphosphonate

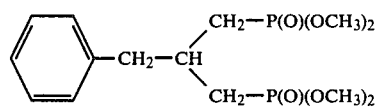

A suspension of 3.6 g (12.2 mmol) f 2-benzyl-1,3-propylidene diphosphonic acid in 13 g (123 mmol) trimethyl orthoformate was refluxed with stirring for 90 minutes. The methanol and methyl formate that were produced were distilled off, thereby allowing the reaction temperature to increase. Removal of volatile products was continued until the acid dissolved in the reagent and trimethyl orthoformate began to distill. The whole procedure was repeated with addition of a fresh amount (13 g) trimethyl orthoformate. Thin layer chromatography (Silica gel, 95:5 chloroform:methanol mixture) was employed to verify that the methylation process was completed. After removal of excess trimethyl orthoformate the residue was submitted to ball tube distillation to give 2.4 g (58% yield) of tetramethyl 2-benzyl-1,3-propylidenediphosphonate as a colorless oil.

bp=150°-152° (0.05 mm Hg)

IR (liquid film): 3030 cm$^{-1}$: aromatic C—H; 2960: aliphatic C—H; 1240: P=O; 1185: P—O—Me; 1030: P—O—C; 800: aromatic C—H NMR (CDCl$_3$): δ=7.3-7.16 (multiplet, 5H); aromatic H; 3.7 (doublet, J=11 Hz, 12H): P—O—C$\underline{H}_3$; 2.85 (doublet, J=7 Hz, 2H): Ph—C$\underline{H}_2$—CH; 2.55-2.35 (multiplet, 1H): Ph—CH$_2$—C$\underline{H}$; 2.03 (doublet of doublet of doublet, J=7, 16 and 19 Hz, 2H): diastereotopic H$^a$: —C($\underline{H}^a$)(H$^b$)—PO$_3$Me$_2$; 1.85 (distorted doublet of doublet of doublet, 2H): diastereotopic H$^b$: —C(H$^a$)($\underline{H}^b$)—PO$_3$Me$_2$

EXAMPLE 5

Tetraisopropyl 2-benzyl-1,3-propylidenephosphonate

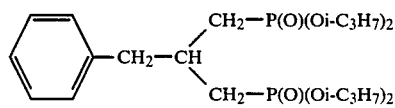

The title compound was prepared by reacting a solution of 10.6 g (22 mmol) ditosylate of 2-benzyl-1,3-propanediol in 25 ml dioxane with 25 ml of a 3.5 Molar solution of sodium diisopropyl phosphite in tetrahydrofuran. After work up of the reaction, ball tube distillation yielded 5.5 g (54% yield) of tetraisopropyl 2-benzyl-1,3-propylidenediphosphonate as a colorless oil.

The title compound was also prepared by heating at 180° for six hours a mixture of 1.8 g (6 mmol) 2-benzyl-1,3-dibromopropane and 14.2 g (60 mmol) triisopropyl phosphite. Distillation gave 1.9 g (70%) of pure tetraisopropyl 2-benzyl-1,3-propylidenediphosphonate.

bp=160°-165°/0.05 mm Hg

IR (liquid film): 3040 cm$^{-1}$: aromatic C—H; 2980+2940: aliphatic C—H; 1390+1380: isopropyl group; 1240: P=O; 990: P—O—C NMR (CDCl$_3$): δ=7.3-7.15 (multiplet, 5H), Aromatic H; 4.65 (finely split septet, J=7 Hz, 4H): PO$_3$(CH Me$_2$)$_2$; 2.90 (doublet, J=7 Hz, 2H): Ph—CH$_2$—CH; 2.55-2.40 (multiplet, 1H): Ph—CH$_2$—CH; 2.0 (doublet of doublet, J=7, 16 and 19 Hz, 2H): diastereotopic H$^a$: C(H$^a$)(H$^b$)—PO$_3$iPr$_2$; 1.75 (finely split doublet of doublet of doublet): diastereotopic H$^b$: C(H$^a$)(H$^b$)—PO$_3$iPr$_2$; 1.25-1.35 (several overlapped doublets, J=7 Hz, 24H): PO$_3$(CH—(CH$_3$)$_2$)$_2$

EXAMPLE 6

Tetrabutyl 2-benzyl-1,3-propylidenediphosphonate

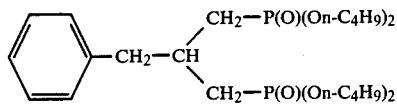

A 2.0 Molar solution of sodium dibutyl phosphite in tetrahydrofuran was prepared according to the procedure described for sodium diethyl phosphite.

A solution of 15 g (32 mmol) ditosylate of 2-benzyl-1,3-propanediol in 40 ml dioxane was added to 40 ml of 2 Molar solution of sodium dibutyl phosphite in tetrahydrofuran. A voluminous precipitate of sodium tosylate separated out when the mixture was heated to 80°. This temperature was maintained for 15 hours then the reaction mixture was concentrated under vacuum and the residue was partitioned between chloroform and water. The organic phase was evaporated and the residue was purified by ball tube distillation. Tetrabutyl 2-benzyl-1,3-propylidenephosphonate was obtained as a colorless oil (10.0 g, 60% yield).

The same compound was obtained when 8.8 g (30 mmol) 2-benzyl-1,3-dibromopropane was reacted with 50 ml of a toluene solution containing 120 mmol of sodium dibutyl phosphite and the mixture was refluxed for 5 hours. Tetrabutyl 2-benzyl-1,3-propylidenediphosphonate was obtained at 55% yield.

bp=175°-180° (0.05 mm Hg)

IR (liquid film): 3040 cm$^{-1}$: aromatic C—H; 2960+2940: aliphatic C—H; 1600+1500: aromatic C—C; 1240: P=O; 1070, 1020+980: P—O—C NMR (CDCl$_3$): δ=7.3-7.15 (multiplet, 5H): Aromatic H; 4.06-3.94 (multiplet, 8H): P—O—CH$_2$—CH$_2$—CH$_2$CH$_3$); 2.90 (doublet, J=7 Hz, 2H): Ph—CH$_2$—CH; 2.55-2.4 (multiplet, 1H): Ph—CH$_2$—CH; 2.02 (doublet of doublet of doublet, J=7, 16 and 19 Hz, 2H): diastereotopic H$^a$: C(H$^a$)(H$^b$)—PO$_3$Bu$_2$; 1.85 (distorted doublet of doublet of doublet, 2H): diastereotopic H$^b$: C(H$^a$)(H$^b$)—PO$_3$Bu$_2$; 1.42 (multiplet, 8H): P—O—CH$_2$—CH$_2$—CH$_2$—CH$_3$; 1.36 (sextet, J=7 Hz, 8H): P—O—CH$_2$—CH$_2$—CH$_2$—CH$_3$; 0.90 (triplet, J=7 Hz, 12H): P—O—CH$_2$—CH$_2$—CH$_2$—CH$_3$

EXAMPLE 7

2-(2-Phenoxyethyl)-1,3-propylidenediphosphonic acid

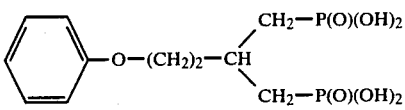

An amount of 3.40 g (7.8 mmol) of tetraethyl 2-(2-phenoxyethyl)-1,3-propylidenediphosphonate prepared exactly according to conditions described in example 1 of this application was dissolved in 5 ml chloroform and trimethyl bromosilane (5.9 g, 38.5 mmol) was added dropwise. The reaction mixture protected by a CaCl$_2$ tube is stirred at room temperature for 15 hours then hydrolysis was carried out by adding 20 ml of water. Evaporation of the aqueous phase gave 2.5 g (100% yield) of a white powder of 2-(2-phenoxyethyl)-1,3-propylidenediphosphonic acid.

mp=149°-153°

IR (KBr): 2900+2350 cm$^{-1}$ (broad): P—O—H; 1600+1500: aromatic C—C; 1250+1130: P=O; 1000+950: P—OH

EXAMPLE 8

Tetrabutyl 2-(3-phenylpropyl)-1,3-propylidenediphosphonate

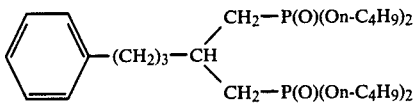

Diethyl malonate (211 g, 1.32 mol) was added to a solution of 30.3 g (1.32 mmol) sodium in 1500 ml anhydrous ethanol. 3-Phenylpropyl bromide (249 g, 1.25 mol) was then added to the above solution and the resulting mixture was maintained at 60° under stirring for 15 hours. The ethanol volume was reduced under vacuum and the residue was partitioned between water and dichloromethane. The dried organic phase was evaporated to give 282 g diethyl 3-phenylpropyl malonate (80% yield).

bp=110°-115° (0.05 mm Hg)

IR (film)=1750 and 1730 cm$^{-1}$ (C=O), 1300-1150 (C—O)

The above compound (170 g, 0.61 mmol) was then added dropwise to a suspension of 25.8 g (0.68 mol) LiAlH$_4$ in 650 ml ether and the reaction mixture was refluxed for 15 hours. The excess of LiAlH$_4$ was destroyed by successive additions of 50 ml ethyl acetate, 40 ml water and finally 850 ml 15% sulfuric acid. The ether phase was evaporated to dryness and the residue was recrystallized in an ether:petroleum ether mixture, yielding 58 g (49%) of 2-(3-phenylpropyl)-1,3-propanediol.

mp=35°-37°

IR (KBr)=3300 cm$^{-1}$ (OH), 1030 (C—O) A solution of the above diol (57.5 g, 0.296 mol) in 50 ml dry pyridine was added at 0° to a solution of 135 g (0.71 mol) tosyl chloride dissolved in 250 ml dry pyridine. The reaction mixture was stirred at room temperature overnight and then was poured on 500 ml ice-water. The separated viscous mass was recrystallized in an acetone: petroleum ether mixture to give 96 g (65%) of ditosylate of 2-(3-phenylpropyl)-1,3-propanediol.

mp=54°-56°

IR (KBr)=1360 and 1170 cm$^{-1}$ (—SO$_2$—)

A solution of sodium dibutyl phosphite was prepared by adding 60 g (0.31 mol) dibutyl phosphite to a suspension of 9.0 g (0.30 mol) 80% dispersion sodium hydride in mineral oil in 100 ml tetrahydrofuran. To this reagent there was added a solution of 51 g (0.10 mol) ditosylate of 2-(3-phenylpropyl)-1,3-propanediol in 100 ml dioxane. After 15 hours at 80° to the reaction mixture was concentrated under vacuum and the residue was partitioned between dichloromethane and water. The dried organic phase is evaporated and the oily residue was purified by ball-tube distillation to give 39 g (70%) of tetrabutyl 2-(3-phenylpropyl)-1,3-propylidene diphosphonate.

bp=185°-190° (0.05 mm Hg)

Elemental analysis C$_{28}$H$_{52}$O$_6$P$_2$: Theor: % C 61.54; % H 9.52; % P 11.36; Found: % C 61.26; % H 9.72; % P 11.54 IR (liquid film)=3040 cm$^{-1}$: aromatic C—H; 2970: aliphatic C—H; 1600+1500: aromatic C—C; 1240: P=O; 1070+1040: P—O—C NMR (CDCl$_3$): δ=7.3-7.15 (multiplet, 5H): Aromatic H; 4.05-3.95 (multiplet, 8H): P—O—CH$_2$—CH$_2$—CH$_2$—CH$_3$; 2.60 (triplet, J=7 Hz, 2H): Ph—CH$_2$—CH$_2$—CH$_2$; 2.34-2.17 (multiplet, 1H): Ph—(CH$_2$)$_3$—CH—; 2.03 (doublet of doublet of doublet, J=7, 16 and 19 Hz, 2H): diastereotopic H$^a$: C(H$^a$) (H$^b$)—PO$_3$Bu$_2$; 1.84 (distorted doublet of doublet of doublet, 2H): diastereotopic H$^b$: C(H$^a$) (H$^b$)—PO$_3$Bu$_2$; 1.70-1.58 (multiplet, 12H): Ph—CH$_2$—(CH$_2$)$_2$+P—O—CH$_2$—CH$_2$CH$_3$; 1.40 (sextet, J=7 Hz, 8H): P—O—CH$_2$—CH$_2$—CH$_2$—CH$_3$; 0.92 (triplet, J=7 Hz, 12H): P—O—CH$_2$—CH$_2$—CH$_2$—CH$_3$

EXAMPLE 9

Tetrabutyl 2-(3-Cyclohexylpropyl)-1,3-propylidenediphosphonate

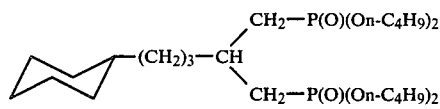

3-Cyclohexylpropyl chloride (70 g, 0.44 mol) was reacted with a solution of 0.64 mol sodium diethyl malonate in ethanol (270 ml) at 60° for 15 hours. An amount of 62 g (50%) of diethyl 3-cyclohexylpropyl malonate was obtained.

bp=117°-125° (0.05 mm Hg)

IR (film)=1730 cm$^{-1}$ (C=O), 1300-1100 (C—O)

The above compound (20 g, 70 mmol) was reacted with a suspension of LiAlH$_4$ (3.5 g, 92 mmol) in 80 ml dry tetrahydrofuran at reflux temperature for 4 hours. The reaction volume was reduced and the residue was diluted with 150 ml ether. The excess of LiAlH$_4$ was destroyed by 6 ml water and 100 ml 15% H$_2$SO$_4$. Evaporation of the dried ether phase gave 9 g (49%) of 2-(3-cyclohexylpropyl)-1,3-propanediol.

mp=47°-48°

IR(KBr)=3250 cm$^{-1}$ (OH), 1030 (C—O)

The above diol (8 g, 40 mmol) was reacted with tosyl chloride (19.1 g, 100 mmol) in pyridine (40 ml) in the usual manner to afford 18.8 g (92% yield) ditosylate of 2-(3-cyclohexylpropyl)1,3-propanediol.

mp=68°-70°

IR (KBr)=1350 and 1170 cm$^{-1}$ (—SO$_2$—)

A solution of 8 g (15.7 mmol) of the above ditosylate in a mixture of 20 ml tetrahydrofuran and 80 ml dioxane was reacted at 75° with a solution of 63 mmol sodium dibutyl phosphite in 60 ml tetrahydrofuran. After workup, vacuum distillation gave 6.0 g (69% yield) of tetrabutyl 2-(3-cyclohexylpropyl)-1,3-propylidenediphosphonate.

bp=190°-195°/0.05 mm Hg

IR (KBr)=2960 cm$^{-1}$: aliphatic C—H; 1240: P=O; 1040-980: P—O—C

NMR (CDCl$_3$) : δ=4.1-3.96 (multiplet, 8H): P—O—CH$_2$—CH$_2$—CH$_2$—CH$_3$; 2.33-2.14 (multiplet, 1H): C$_6$H$_{11}$—(CH$_2$)$_3$—CH—; 2.03 (doublet of doublet of doublet, J=7, 16 and 19 Hz, 2H): diastereotopic H$^a$: C(H$^a$) (H$^b$)—PO$_3$Bu$_2$; 1.84 (distorted doublet of doublet of doublet, 2H): diastereotopic H$^b$: C(H$^a$) (H$^b$)—PO$_3$Bu$_2$; 1.74-1.60 (multiplet, 12H): C$_6$H$_{11}$—CH$_2$—(CH$_2$)$_2$-+P—O—CH$_2$—CH$_2$—CH$_2$CH$_3$; 1.6-1.52 (quarter, 2H): C$_6$H$_{11}$—CH$_2$; 1.40 (sextet, J=7 Hz, 8H): P—O—CH$_2$—CH$_2$—CH$_2$—CH$_3$; 1.35-1.10 (large multiplet, 11H): C$_6$H$_{11}$; 0.92 (triplet, J=7 Hz, 12H): P—O—CH$_2$—CH$_2$—CH$_2$—CH$_3$

EXAMPLE 10

Tetrabutyl 2-(2-phenoxyethyl)-1,3-propylidenediphosphonate

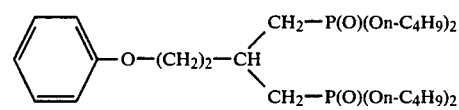

2-Phenoxyethyl bromide (84 g, 0.42 mol) was reacted with a solution of 0.42 mol sodium diethyl malonate in 400 ml ethanol to yield 85 g (72%) of diethyl 2-phenoxyethyl malonate.

bp=130°-140° (0.05 mm Hg)

IR (film): 1730 cm$^{-1}$: (C=O), 1300-1150 (C—O)

The above compound (70 g, 0.25 mol) was reduced by a suspension of 10.92 g (0.28 mol) LiAlH$_4$ in 420 ml dry ether. An amount of 44 g (62%) 2-(2-phenoxyethyl)-1,3-propanediol was obtained.

mp=71°-72°

IR (KBr): 3300 cm$^{-1}$ (OH), 1030 (C—O)

The above diol (30 g, 0.15 mol) was reacted with 80 g (0.46 mol) in tosyl chloride in 180 ml dry pyridine to give 62 g (82%) ditosylate of 2-(2-phenoxyethyl)-1,3-propanediol.

mp=69°-70°

IR (KBr): 1370 and 1170 cm$^{-1}$ (SO$_2$)

To a solution of 190 mmol sodium dibutyl phosphite in 100 ml tetrahydrofuran there was added a solution of the above ditosylate (20 g, 40 mmol) in a mixture of tetrahydrofuran (50 ml) and dioxane (150 ml) and the resulting mixture was heated at 80° overnight. After work up, ball tube distillation gave 12 g (55% yield) of tetrabutyl 2-(2-phenoxyethyl)-1,3-propylidenediphosphonate.

An equivalent yield was obtained when the phosphonation reaction was carried out in dimethoxyethane. A solution of 160 mmol sodium dibutylphosphite in 80 ml dimethoxyethane was prepared by reacting 35.2 g (180 mmol) dibutyl phosphite with 4.8 g (160 mmol) 80% sodium hydride. A solution of 20 g (39.6 mmol) of ditosylate of 2-(2-phenoxyethyl)-1,3-propane diol in 70 ml dimethoxyethane was introduced and the resulting mixture was refluxed overnight. Work-up gave 17.4 g (60% yield) of tetrabutyl 2-(phenoxyethyl)-1,3-propylidenediphosphonate.

bp=205°-210° (0.05 mm Hg)

IR (liquor film): 2970 cm$^{-1}$: aliphatic C—H; 1600: aromatic C—H; 1240: P=O; 1070+980: P—O—C NMR (CDCl$_3$): δ=7.3-7.24 and 6.95-6.85 (multiplet, 5H): Aromatic H; 4.09-3.95 (multiplet, 8H): P—O—C$\underline{H}$$_2$—CH$_2$CH$_3$+PhO—CH$_2$; 2.62-2.44 (multiplet, 1H) : PhO—(CH$_2$)$_2$—CH—; 2.20-2.06 (multiplet, 4H): diastereotopic H$^a$: C($\underline{H^a}$) (H$^b$)—PO$_3$Bu$_2$+PhO—CH$_2$—CH$_2$; 2.0 (distorted doublet of doublet of doublet, 2H): diastereotopic H$^b$: C(H$^a$) ($\underline{H^b}$)—PO$_3$Bu$_2$; 1.63 (quintet, 8H): P—O—CH$_2$—CH$_2$—CH$_2$CH$_3$; 1.40 (sextet, J=7 Hz, 8H): P—O—$\overline{C}$H$_2$—CH$_2$—CH$_2$—CH$_3$; 0.92 (triplet, J=7 Hz, 12H): P—O—CH$_2$—$\overline{C}$H$_2$—CH$_2$—C$\underline{H}$$_3$

EXAMPLE 11

Tetraethyl 2-(1-naphtylmethyl)-1,3-propylidenediphosphonate

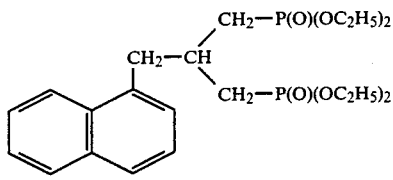

Diethyl malonate (91 g, 0.57 mol) was added to a sodium ethoxide solution prepared by dissolving 13.1 g (0.57 mol) sodium metal in 460 ml anhydrous ethanol. The resulting mixture was stirred at 50° for one hour, then a solution of 100 g (0.57 mol) 1-chloromethyl naphtalene in 50 ml ethanol was added dropwise. A white precipitate of sodium chloride soon separated out. The reaction mixture was heated at 60° overnight. The ethanol mixture was concentrated under vacuum and the residue was partitioned between ether and water. The dried ether solution was evaporated leaving a viscous oil that slowly solidified. Recrystallization in ether yielded 120 g (0.4 mol) of diethyl (1-naphtyl) methylmalonate (70% yield).

mp=27°-28°

IR (KBr): 1750 and 1730 cm$^{-1}$: C=O, 1280-1150 (C—O)

To a suspension of 19.8 g (0.52 mol) lithium aluminium hydride in 500 ml dry ether there was added a solution of 120 g (0.4 mol) diethyl (1-naphtyl) methylmalonate in 80 ml ether and the resulting mixture was refluxed for 12 hours. The excess of LiAlH$_4$ was destroyed by successive additions of 70 ml water and 110 ml 15% H$_2$SO$_4$. The separated ether phase was washed with a saturated sodium bicarbonate solution and dried over MgSO$_4$. After evaporation of ether the solid residue was recrystallized in a 95:5 ether:petroleum ether mixture to give 35 g (0.16 mol) of white crystals of 2-(1-naphtylmethyl)-1,3-propanediol (40% yield).

mp=78°-81°

IR (KBr)=3250 cm$^{-1}$ (OH), 1040 (C—O), 790 (naphtyl C—H)

A solution of 30 g (0.14 mol) 2-(1-naphtylmethyl)-1,3-propanediol in 50 ml pyridine was added at 0° to a solution of 78 g (0.41 mol) tosyl chloride dissolved in 110 ml pyridine. The reaction mixture was stirred at room temperature for 15 hours and then was poured on 500 ml ice water. A viscous semi-solid mass separated out; it was taken up in 50 ml cold ether to give a white solid. Recrystallization in an acetone:petroleum ether mixture afforded 46 g (62% yield) of ditosylate of 2-(1-naphtylmethyl)-1,3-propane diol.

mp=90°-91°

IR (KBr)=1380 and 1180 cm$^{-1}$ (SO$_2$), 830 and 770 (naphtyl C—H)

A solution of 10 g (19 mmol) of the above described ditosylate in 20 ml dioxane was added to a solution containing 65 mmol sodium diethyl phosphite in 20 ml tetrahydrofuran. The reaction mixture was heated at 100° for 3 hours, then the mixture of solvents was removed by evaporation and the residue was partitioned between chloroform and water. Evaporation of the dried organic phase left a viscous oil that was purified by ball tube distillation. Tetraethyl 2-(1-naphtylmethyl)-1,3-propylidenediphosphate (5.2 g, 11.4 mmol) was obtained as a pale yellow viscous oil, (yield=60%).

bp=195°-200° (0.05 mm Hg)

Elemental analysis C$_{22}$H$_{34}$O$_6$P$_2$: Theor.: % C57.89; % H 7.46; % P 13.60; Found: % C 57.92; % H 7.72; % P 13.40

IR (liquid film)=3060 cm$^{-1}$: aromatic C—H; 2990: aliphatic C—H; 1240: P=O; 1060+1040: P—O—C; 800: naphtyl C—H NMR (CDCl$_3$): δ=8.28, 7.83 and 7.73 (three doublets, J=8 Hz, 3H) aromatic protons from the substituted phenyl ring; 7.55-7.26 (multiplet, 4H): aromatic protons from the fused benzo ring; 4.10-3.90 (multiplet, 8H): P—O—CH$_2$—CH$_3$; 3.35 (doublet, J=7 Hz, 2H): C$_{10}$H$_7$—CH$_2$—$\overline{C}$H; 2.75-2.58 (multiplet, 1H): C$_{10}$H$_7$—$\overline{C}$H$_2$—CH; 2.14 (doublet of doublet of doublet, J=7, 16 and 19 Hz, 2H) diastereotopic H$^a$: —C($\underline{H^a}$) (H$^b$)—PO$_3$Et$_2$; 1.87 (distorted doublet of doublet of doublet, 2H): diastereotopic H$^b$: —C(H$^a$) ($\underline{H^b}$)—PO$_3$Et$_2$; 1.24 and 1.18 (two triplets, J=7 Hz, 12H): P—O—CH$_2$—C$\underline{H}$$_3$

EXAMPLE 12

Tetrabutyl 2-[3-(3-pyridyl)propyl]-1,3-propylidenediphosphonate

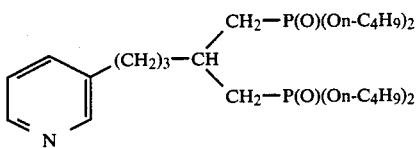

3-(3-Pyridyl)propyl chloride hydrochloride was prepared in quantitative yield by reacting 3-(3-pyridyl)propanol with phosphorus oxychloride in ethyl acetate at reflux temperature. The free base was generated by dissolving the hydrochloride in a 10% sodium hydroxide solution and extracting with an organic solvent (toluene or ether).

Diethyl malonate (156 g, 0.98 mol) was reacted with a solution of 66.5 g (0.98 mol) sodium ethoxide in 400 ml ethanol. An amount of 100 g (0.65 mol) 3-(3-pyridyl)propyl chloride was then added and the reaction mixture was kept at 60° overnight. Ethanol was evaporated and the residue was partitioned between chloroform and water. Ball-tube distillation gave 90 g (50% yield) of diethyl 3-(3-pyridyl)propyl malonate as a slightly yellow oil.

bp=135°-140° (0.05 mm Hg)

IR (film): 1720 cm$^{-1}$ (C=O), 1300–1150 (C—O)

An amount of 20 g (72 mmol) of the above malonate was added dropwise to a suspension of 3.9 g (103 mmol) LiAlH$_4$ in 70 ml dry tetrahydrofuran and the reaction mixture was refluxed for 4 hours. The excess of LiAlH$_4$ was destroyed by addition of 8 ml water and the precipitated hydroxides were filtered off. Evaporation of tetrahydrofuran gave 11.5 g of an orange oil that was purified by column chromatography (silicagel, 8:2 chloroform: methanol mixture). An amount of 7.7 g (55% yield) of 2-[3-(3-pyridyl)propyl]-1,3-propane diol was obtained.

mp=45°–48°

IR (KBr): 3300 cm$^{-1}$ (OH), 1020 (C—O)

An amount of 18.4 g (96.6 mmol) tosyl chloride dissolved in 30 ml dry pyridine was added to a solution of 6.3 g (32.3 mmol) of the above diol in 20 ml pyridine then the reaction mixture was stirred at 0° overnight. The crystals of pyridinium hydrochloride were filtered off then the pyridine solution was poured while stirring on 500 ml of ice-water. The separated solid was recrystallized in an acetone:ether mixture to yield 9.8 g (60%) of ditosylate of 2-[3-(3-pyridyl)propyl]propane 1,3-diol.

mp=85°–86°

IR (KBr)=1360 and 1170 cm$^{-1}$ (—SO$_2$—)

To a solution containing 28.8 mmol sodium dibutyl phosphite in 20 ml tetrahydrofuran there was added a solution of the above ditosylate (3.4 g, 6.8 mmol) in a mixture of tetrahydrofuran (10 ml) and dioxan (30 ml). The reaction mixture was heated at 90°, whereupon sodium tosylate separates out. After 15 hours at 90°, the reaction mixture was partitioned between water and chloroform. Evaporation of the dried organic phase was followed by heating the oil up to 150° under a 0.05 mm Hg vacuum to remove the volatile materials. The residue was purified by passing through a silicagel column using a 9:1 chloroform: methanol mixture as eluent. An amount of 2.8 g (75% yield) of tetrabutyl 2-[3-(3-pyridyl)propyl]-1,3-propylidenediphosphonate was obtained as a slightly yellow oil.

IR (liquid film)=2970 cm$^{-1}$: aliphatic C—H; 1240: P=O; 1020+980: P—O—C

NMR (CDCl$_3$): δ=8.46, 7.6 and 7.3 (multiplets, 4H): Heteroaromatic H; 4.05–3.95 (multiplet, 8H): P—O—C$\underline{H}_2$—CH$_2$—CH$_2$—CH$_3$; 2.65 (triplet, J=7 Hz, 2H): C$_5$H$_4$N—C$\underline{H}_2$—CH$_2$—CH$_2$; 2.35–2.0 (multiplet, 1H): C$_5$H$_4$N—(CH$_2$)$_3$—C$\underline{H}$—; 2.03 (doublet of doublet of doublet, J=7, 16 and 19 Hz, 2H): diastereotopic H$^a$: C($\underline{H}^a$)(H$^b$)—PO$_3$Bu$_2$; 1.84 (distorted doublet of doublet of doublet, 2H): diastereotopic H$^b$: C(H$^a$)($\underline{H}^b$)—PO$_3$Bu$_2$; 1.72–1.60 (multiplet, 12H): C$_5$H$_4$N—CH$_2$—(C$\underline{H}_2$)$_2$+P—O—CH$_2$—C$\underline{H}_2$—CH$_2$CH$_3$; 1.40 (sextet, J=7 Hz, 8H): P—O—CH$_2$—CH$_2$—C$\underline{H}_2$—CH$_3$; 0.95 (triplet, J=7 Hz, 12H): P—O—CH$_2$—CH$_2$—CH$_2$—C$\underline{H}_3$ Hydrogen chloride gas was introduced into a solution of the above compound in dry diethyl ether. Evaporation of the solvent gave the hydrochloride salt of tetrabutyl 2-[3-(3-pyridyl)propyl]-1,3-propylidenediphosphonate.

IR=2970 cm$^{-1}$: aliphatic C—H; 2500–2200: N—H ammonium salt; 1240: P=O; 1020+980: P—O—C

EXAMPLE 13

Tetrapentyl 2-(3-phenylpropyl)-1,3-propylidenediphosphonate

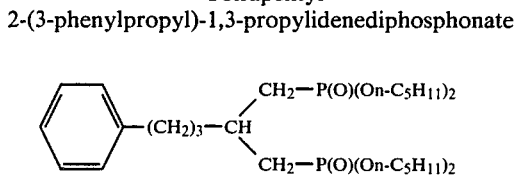

A solution of sodium dipentyl phosphite was prepared by adding 80 g (0.36 mol) di n-pentyl phosphite to a suspension of 8.6 g (0.29 mol) 80% sodium hydride in 150 ml tetrahydrofuran followed by heating the mixture at 60° until total consumption of sodium hydride. To this solution were added 40 g (0.08 mol) ditosylate of 2-(3-phenylpropyl)-1,3-propanediol dissolved in 150 ml dioxane and the resulting mixture was heated at 80° C. overnight. After work up of the reaction, ball-tube distillation afforded 38 g (79%) of tetrapentyl 2-(3-phenylpropyl)-1,3-propylidenediphosphonate.

bp=210°–215° (0.05 mm Hg)

IR (liquid film): 3050 cm$^{-1}$: aromatic C—H; 2960: aliphatic C—H; 1240: P=O; 1050+1000: P—O—C NMR (CDCl$_3$): δ=7.3–7.15 (multiplet): Aromatic H; 4.05–3.95 (multiplet, 8H): P—O—CH$_2$—C$_4$H$_9$; 2.60 (triplet, J=7 Hz, 2H): Ph—C$\underline{H}_2$—(C$\underline{H}_2$)$_2$; 2.35–2.18 (multiplet, 1H): Ph(CH$_2$)$_3$—C$\underline{H}$; 2.05 (doublet of doublet of doublet, J=7, 16 and 19 Hz, 2H): diastereotopic H$^a$: C($\underline{H}^a$)(H$^b$)—PO$_3$(C$_5$H$_{11}$)$_2$; 1.85 (distorted doublet of doublet of doublet, 2H): diastereotopic H$^b$: C(H$^a$)($\underline{H}^b$)—PO$_3$(C$_5$H$_{11}$)$_2$; 1.65 (multiplet, 12H): Ph—CH$_2$(C$\underline{H}_2$)$_2$+P—O—CH$_2$—C$\underline{H}_2$—C$_3$H$_7$; 1.35 (multiplet, 16H): P—O—(CH$_2$)$_2$—(C$\underline{H}_2$)$_2$—CH$_3$; 0.92 (distorted triplet, J=7 Hz, 12H): P—O—(CH$_2$)$_4$—C$\underline{H}_3$

EXAMPLE 14

Tetrahexyl 2-(3-phenylpropyl)-1,3-propylidenediphosphonate

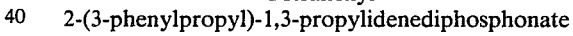

The title compound was prepared by reacting a solution of 20 g (0.04 mol) ditosylate of 2-(3-phenylpropyl)-1,3-propanediol dissolved in 80 ml dioxane with a solution of sodium dihexyl phosphite obtained by reacting 4.2 g (0.14 mol) 80% sodium hydride with 40 g (0.16 mol) dihexyl phosphite in 80 ml tetrahydrofuran. Ball-tube distillation afforded 11 g (42%) tetrahexyl 2-(3-phenylpropyl)-1,3-propylidenediphosphonate.

bp=225°–230° (0.05 mm Hg)

IR (liquid film): 3040 cm$^{-1}$: aromatic C—H; 2960: aliphatic C—H; 1240: P=O; 1050-990: P—O—C NMR (COCl$_3$): δ=7.3–7.15 (multiplet): Aromatic H; 4.05–3.95 (multiplet, 8H): P—O—CH$_2$—C$_5$H$_{11}$; 2.63 (triplet, J=7 Hz, 2H): Ph—C$\underline{H}_2$—(C$\underline{H}_2$)$_2$; 2.35–2.20 (multiplet, 1H): Ph—(CH$_2$)$_3$—C$\underline{H}$; 2.04 (doublet of doublet of doublet, J=7, 16 and 19 Hz, 2H): diastereotopic H$^a$: C($\underline{H}^a$)(H$^b$)—PO$_3$(C$_6$H$_{13}$)$_2$; 1.85 (distorted doublet of doublet of doublet, 2H): diastereotopic H$^b$: C(H$^a$)($\underline{H}^b$)—PO$_3$(C$_6$H$_{13}$)$_2$; 1.65 (multiplet, 12H): Ph—C$\underline{H}_2$—(C$\underline{H}_2$)$_2$+P—O—CH$_2$C$\underline{H}_2$—C$_4$H$_9$; 1.42–1.26 (large multiplet, 24H):

P—O—(CH$_2$)$_2$—(CH$_2$)$_3$—CH$_3$; 0.90 (distorted triplet, J=7 Hz, 12H): P—O—(CH$_2$)$_5$—C$\underline{H}$$_3$

EXAMPLE 15

Tetrakis [2-(N,N-dimethylamino)ethyl] 2-benzyl-1,3-propylidenediphosphonate

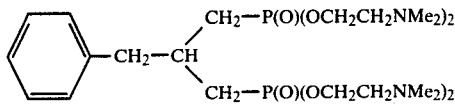

An amount of 58 g (379 mmol) bromotrimethylsilane was added dropwise to 25.7 g (63 mmol) tetraethyl 2-benzyl-1,3-propylidenediphosphonate under anhydrous conditions and the resulting mixture was stirred at room temperature overnight. The excess of reagent was removed, then the residue was distilled to give 23.3 g (63%) of tetrakis (trimethylsilyl) 2-benzyl-1,3-propylidenediphosphonate.

bp=168°-175° (0.05 mm Hg)

IR (liquid film)=3080+3040 cm$^{-1}$: aromatic C—H; 2970: C—H; 1260: P=O+CH$_3$—Si; 1040: P—O—Si; 850+740: CH$_3$—Si A solution of 20 g (34 mmol) of the above compound in 50 ml carbon tetrachloride was added under anhydrous conditions to a suspension of 28.7 g (137 mmol) phosphorus pentachloride in 150 ml carbon tetrachloride. The turbid reaction mixture was heated at 60° for 15 hours whereupon it became a clear solution. The volatile materials (chlorotrimethylsilane and phosphorus oxychloride) were distilled off and the residue was purified by ball-tube distillation. An amount of 10.8 g (85%) of 2-benzyl-1,3-propylidenediphosphonyl tetrachloride was obtained.

bp=175° (0.05 mm Hg)

IR (liquid film)=3040 cm$^{-1}$: aromatic C—H; 2960: aliphatic C—H; 1270: P=O; 560: P—Cl A solution of 20.8 g (234 mmol) 2-(N,N-dimethylamino) ethanol in 40 ml chloroform was added dropwise to a solution of 10.7 g (25 mmol) of the above compound in 70 ml chloroform at 0°. A white precipitate soon separated out. The reaction mixture was stirred at room temperature for 48 hours. The mixture was diluted with 40 ml chloroform and extracted by 60 ml water. The organic phase was twice extracted with 60 ml saturated NaCl solution, dried and the solvent was evaporate. The residue was heated at 70° under a 0.05 mm Hg vacuum to remove the excess of dimethylaminoethanol.

Further purification was carried out by dissolving the crude compound in 250 ml dichloromethane and extracting it with two portions of cold 15% HCl solution. The acid aqueous phase was neutralized to pH 10 with a 5% NaOH solution and back-extracted with three portions of 40 ml dichloromethane. Evaporation of the dried solvent left 5.0 g (30%) of tetrakis [2-(N,N-dimethylamino)ethyl] 2-benzyl-1,3-propylidenediphosphonate as a viscous oil.

IR (liquid film): 2970 cm$^{-1}$: aliphatic C—H; 2820+2770: N-methyl group; 1460: CH$_2$—; 1240: P=O; 1030+950: P—O—C; 790: aromatic C—H NMR (CDCl$_3$): δ=7.34-7.20 (multiplet, 5H): aromatic H; 4.20-4.04 (multiplet, 8H): P—O—C$\underline{H}$$_2$—CH$_2$—NMe$_2$; 2.90 (doublet, J=7 Hz, 2H): Ph—C$\underline{H}$$_2$—CH; 2.56 (triplet, J=7 Hz, 8H): P—O—CH$_2$—C$\underline{H}$$_2$—NMe$_2$; 2.50 (partially overlapped multiplet, 1H): Ph—CH$_2$—C$\underline{H}$; 2.25 (singlet, 24H): —NMe$_2$; 2.10 (doublet of doublet of doublet, J=7, 16 and 19 Hz, 2H): diastereotopic H$^a$: C(H$^a$)(H$^b$)—PO$_3$; 1.84 (distorted doublet of doublet of doublet, 2H): diastereotopic H$^b$: C(H$^a$)(H$\underline{^b}$)—PO$_3$

EXAMPLE 16

Bis(ethyl, pentyl) 2-(3-phenylpropyl)-1,3-propylidenediphosphonate

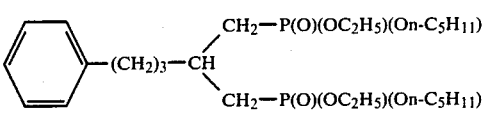

An amount of 44.1 g (0.5 mol) of pentanol was slowly added to 103.0 g (0.75 mol) of PCl$_3$ cooled at $-10°$ C. The hydrogen chloride gas formed was driven out of the reaction mixture by a stream of nitrogen and the solution was stirred for an additional hour at room temperature. Water pump vacuum was then applied to remove the residual gas and 50 g (53%) of pentyl dichlorophosphite were distilled at 66°-70° (15 mm Hg).

IR (liquid film): 2930 cm$^{-1}$: aliphatic C—H; 1000: P—O—C 39.0 g (0.21 mol) of pentyl dichlorophosphite in 10 ml of anhydrous ether were added dropwise to a solution of 19.0 g (0.41 mol) of ethanol in 90 ml of ether maintained below +5° in an ice bath. The mixture was stirred overnight at room temperature. The ether solvent was evaporated and the residue distilled under vacuum. 10.0 g (27%) of ethyl pentyl phosphite were isolated.

bp=85°-100° (15 mm Hg);

IR (liquid film): 2930 cm$^{-1}$: aliphatic C—H; 1250: P=O; 970: P—O—C;

MS: m/e=179 (M$^+$ − 1); 83 (base peak)

To a solution of sodium ethyl pentyl phosphite prepared from 5.76 g (32 mmol) of ethyl pentyl phosphite and 0.90 g (30 mmol) of 80% dispersion sodium hydride in mineral oil in 40 ml anhydrous tetrahydrofuran there was added a solution of 4.0 g (8 mmol) ditosylate of 2-(3-phenylpropyl)-1,3-propanediol in 40 ml anhydrous dioxane. After 15 hours on reflux, the reaction was concentrated under vacuum and the residue was partitioned between chloroform and water. The dried organic phase was evaporated and the residue was fractionated by ball-tube distillation to give 0.5 g (12%) of bis(ethyl, pentyl) 2-(3-phenylpropyl)-1,3-propylidenediphosphonate.

bp=195°-200° (0.05 mm Hg)

IR (liquid film): 3040 cm$^{-1}$: aromatic C—H; 2930: aliphatic C—H; 1240: P=O; 1020: P—O—C NMR (CDCl$_3$): δ=7.3-7.15 (multiplet, 5H): aromatic H; 4.15-4.05 (multiplet, 4H): P—O—C$\underline{H}$$_2$—CH$_3$; 4.05-3.95 (multiplet, 4H): P—O—C$\underline{H}$$_2$—(CH$_2$)$_3$—CH$_3$; 2.60 (triplet, 2H): Ph—CH$_2$—C$\underline{H}$$_2$—CH$_2$; 2.35-2.20 (multiplet, 1H): Ph—(CH$_2$)$_3$—C$\underline{H}$; 2.03 (doublet of doublet of doublet, 2H): diastereotopic H$^a$: C($\underline{H}$$^a$)(H$^b$)—P(O)(OC$_2$H$_5$)(OC$_5$H$_{11}$); 1.85 (distorted doublet of doublet of doublet, 2H): diastereotopic H$^b$=C(H$^a$)($\underline{H}$$^b$)—P(O)(OC$_2$H$_5$)(OC$_5$H$_{11}$); 1.65 (multiplet, 8H)=PhCH$_2$—(CH$_2$)$_2$—CH- +P—OCH$_2$CH$_2$(C$\underline{H}$$_2$)$_2$CH$_3$; 1.35 (multiplet, 8H)=P—O—CH$_2$CH$_2$(CH$_2$)$_2$—CH$_3$; 1.16 (triplet, 6H)=P—O—CH$_2$—C$\underline{H}$$_3$; 0.92 (triplet, 6H)=P—O—(CH$_2$)$_4$—C$\underline{H}$$_3$ MS: m/e=518 (M+); 179 (—P(O)(OC$_2$H$_5$)(OC$_5$H$_{11}$))

EXAMPLE 17

Bis(ethyl, pentyl) 2-benzyl-1,3-propylidenediphosphonate

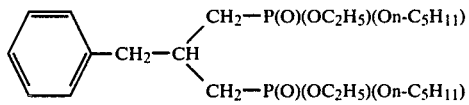

A solution of 25.0 g (0.132 mol) of pentyl dichlorophosphite in 50 ml hexane was added dropwise to a stirred solution of 12.2 g (0.265 mol) ethanol and 20.9 g (0.265 mol) pyridine in 100 ml hexane. The mixture was kept during the addition below 10° by an ice bath. The stirring was continued for an additional 3 hours at room temperature. The voluminous pyridine hydrochloride salt formed was then filtered, washed with hexane and the filtrate concentrated to dryness. The residue was fractionated with a short Vigreux column and 8.0 g (29%) of diethyl pentyl phosphite was collected.

bp=85°-93° (15 mm Hg)

IR (liquid film): 2940 cm$^{-1}$: Aliphatic C—H; 1030: P—O—C

The preparation of 2-benzyl-1,3-dibromopropane is described in example 1.

A mixture of 1.0 g (3.4 mmol) 2-benzyl-1,3-dibromopropane and 3.6 g (17.0 mmol) diethyl pentyl phosphite was refluxed under nitrogen at 180° for 4 hours. The resulting reaction mixture was fractionated by ball tube distillation and 0.4 g (24%) of bis(ethyl, pentyl) 2-benzyl-1,3-propylidenediphosphonate was isolated.

bp=186°-190° (0.05 mm Hg)

IR(liquid film): 2960 cm$^{-1}$: Aliphatic C—H; 1250: P=O; 1050: P—O—C

NMR (CDCl$_3$): δ=7.32-7.18 (multiplet, 5H): aromatic H; 4.15-4.00 (multiplet, 4H): P—O—CH$_2$—CH$_3$; 4.00-3.90 (multiplet, 4H): P—O—CH$_2$—(CH$_2$)$_3$—CH$_3$; 2.90 (doublet, 2H): Ph—CH$_2$—CH; 2.50 (multiplet, 1H): Ph—CH$_2$—CH; 2.03 (doublet of doublet of doublet, 2H): asterereotopic H$^a$: C(H$^a$)(H$^b$)—P(O)(OC$_2$H$_5$)(OC$_5$H$_{11}$); 1.85 (distorted doublet of doublet of doublet, 2H): diastereotopic H$^b$: C(H$^a$)(H$^b$)—P(O)(OC$_2$H$_5$)(OC$_5$H$_{11}$); 1.65 (multiplet, 4H): P—O—CH$_2$CH$_2$(CH$_2$)$_2$CH$_3$; 1.35 (multiplet, 8H): P—O—CH$_2$CH$_2$(CH$_2$)$_2$CH$_3$; 1.30 (triplet, 6H): P—O—CH$_2$—CH$_3$; 0.90 (triplet, 6H): P—O—(CH$_2$)$_4$—CH$_3$ MS: m/e=490 (M+)

EXAMPLE 18

Bis(methyl, hydrogen) 2-benzyl-1,3-propylidenediphosphonate

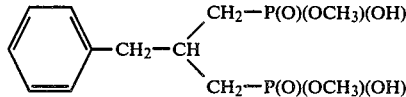

A mixture of 1 g (2.86 mmol) tetramethyl benzyl-2 1,3-propylidenediphosphonate and 6 ml 20% NaOH (15 mmol) was refluxed for 2 hours. After cooling the mixture was acidified by conc. HCl and evaporated to dryness. The residue was taken up in absolute ethanol, filtered and the solution was evaporated to yield 720 mg of bis(methyl, hydrogen) 2-benzyl-1,3-propylidenediphosphonate, yield 78%.

IR: 2900+2300 cm$^{-1}$ (broad): PO—H; 1600: P0—H; 1240: P=O; 1030: P—O—C+P—OH

EXAMPLE 19

Bis(butyl, ethyl) 2-(3-phenylpropyl)-1,3-propylidenediphosphonate

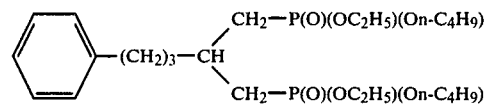

Tetrabutyl 2-(3-phenylpropyl)-1,3-propylidenediphosphonate (10 g, 18 mmol), dissolved in 120 ml of a 7% NaOH solution in n-butanol was heated at 60° for two hours. The solvent was evaporated and the residue partitioned between water and dichloromethane. The organic phase was evaporated and the residue was taken up in 15 ml of a 20% HCl solution. The acid aqueous solution solution was evaporated, 20 ml ethanol was added and the mixture was filtered to remove NaCl. Evaporation of the solvent gave 6.0 g (77% yield) of bis(butyl, hydrogen) 2-(3-phenylpropyl)-1,3-propylidenediphosphonate.

IR=2900+2300 (broad): PO—H; 1600:PO—H; 1240: P=O; 1030: P—O—C+P—OH

The above compound (5 g, 11.5 mmol) was dissolved in 10 ml CH$_2$Cl$_2$ and a five-fold excess of a solution of diazoethane in ether were added. After 1 hour at room temperature, evaporation of the solvent gave pure (GLC) bis(butyl, ethyl) 2-(3-phenylpropyl)-1,3-propylidenediphosphonate (5.6 g, 100% yield).

bp=195°-200° (0.05 mmHg)

IR (film)=2960 cm$^{-1}$: aliphatic C—H; 1250: P=O; 1050-980: P—O—C

When bis(butyl, hydrogen) 2-(3-phenylpropyl)-1,3-propylidenediphosphonate (5 g, 11.5 mol) was reacted with triethyl orthoformate according to the procedure described in example 4, 4.2 g (75% yield) of bis(butyl, ethyl) 2- (3-phenylpropyl)-1,3-propylidenediphosphonate were obtained.

bp=195°-200° (0.05 mmHg)

Thin layer and gas liquid chromatographies showed this compound to be identical to the product obtained by reaction of bis(butyl, hydrogen) 2-(3-phenylpropyl)-1,3-propylidenediphosphonate with diazoethane.

EXAMPLE 20

Tetrabutyl 2-[3-(2,4-dinitrophenyl)propyl]-1,3-propylidenediphosphonate

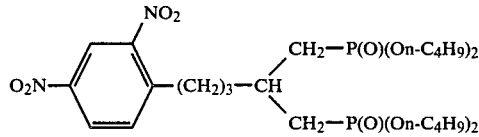

To a mixture of 2 ml concentrated H$_2$SO$_4$ and 2 ml HNO$_3$ cooled to 0° were added 2.5 g (4.6 mmol) tetrabutyl2-(3-phenylpropyl)-1,3-propylidenediphosphonate and the mixture was stirred at 0° for 1 hour. Water was added and the mixture was extracted into benzene. Gas liquid chromatography analysis of the benzene phase to showed that the starting compound has reacted to yield a mixture of these components. Preparative GLC (3% Silar column, temperature program from 120° to 280°) yielded 1.0 g (34% yield) of the main compound identified by combined spectroscopies as tetrabutyl 2-[3-(2,4-dinitrophenyl)propyl]-1,3-propylidenediphosphonate.

MS: m/e=636 (M+)

IR (film): 1350+1550 cm$^{-1}$: —NO$_2$

NMR (CDCL$_3$): δ=8.75, 8.36 and 7.64: (3H): aromatic protons; 4.06-3.95: (multiplet, 8H) P—O—C$\underline{H}_2$CH$_2$CH$_2$CH$_3$; 3.0 (triplet, 2H): Ph—C$\underline{H}_2$—; 2.35-2.2 (multiplet, 1H): C$\underline{H}$—(CH$_2$—PO$_3$Bu$_2$)$_2$; 2.05 (doublet of doublet of doublet, 2H): C($\underline{H}^a$)(H$^b$)—PO$_3$Bu$_2$; 1.85 (doublet of doublet of doublet, 2H): C(H$^a$)($\underline{H}^b$) PO$_3$Bu$_2$; 1.8-1.6 (multiplet, 12H): (C$\underline{H}_2$)$_2$—CH—(CH$_2$PO$_3$)$_2$+P—O—CH$_2$—CH$_2$—CH$_2$—C$\underline{H}_3$; 1.35 (sextet, 7 Hz, 8H): P—O—CH$_2$—CH$_2$—C$\underline{H}_2$—CH$_3$; 0.95 (triplet, 7 Hz, 12H): P—O—CH$_2$—CH$_2$—CH$_2$—C$\underline{H}_3$.

EXAMPLE 21

Tetrabutyl 2-[5-(3-hydroxy-4-hydroxymethyl-2-methyl)pyridylmethyl]1,3-propylidenediphosphonate

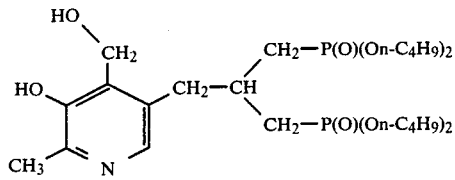

A mixture of 50 g (0.243 mol) pyridoxine hydrochloride in 400 ml dry acetone and 55 ml concentrated H$_2$SO$_4$ was stirred overnight at room temperature. The acid solution was neutralized to pH 7 with sodium hydroxide and evaporated to dryness. The residue was taken up in CHCL$_3$, dried and filtered to give 51.0 g (100% yield) of isopropylidene pyridoxine.

mp: 90°-92°

IR (KBr): 1380 cm$^{-1}$ (doublet): (CH$_3$)$_2$C

A solution of thionyl chloride (77.4 g, 0.65 mol) in 50 ml benzene was added to a warm solution of the above compound (68 g, 0.325 mol in 500 ml benzene) and the mixture was refluxed for 15 min. The precipitate was filtered and recrystallized in an ethanol:ether mixture. The filtered solution of the solid obtained is basified with 15% NaOH, extracted into CHCL$_3$ and dried over potassium carbonate. Evaporation of the solvent gave 30 g (41% yield) of 3,4-isopropylidene 5-(chloromethyl)-3-hydroxy-4-(hydroxymethyl)-2-methyl pyridine. A GLC analysis showed the compound to be pure.

A solution of the above chloride (30 g, 0.132 mol) in 100 ml absolute ethanol was reacted with a sodium diethyl malonate solution (0.132 mol in 120 ml ethanol) for 15 hours. Removal of the excess diethyl malonate left 34.3 g (74% yield) of crude diethyl 5-(3,4-isopropylidene-3-hydroxy-4-hydroxymethyl-2-methyl)-pyridylmethyl malonate.

IR (film): 1740 cm$^{-1}$: C=O; 1200: C—O

The substituted malonate (34.3 g, 98 mmol in 100 ml absolute diethyl ether) was reduced by a suspension of 4.8 g (0.127 mol) LiAlH$_4$ in 250 ml ether. After work-up, trituration of the crude mixture with cold ether gave 9.5 g (36% yield) of 2-[5-(3,4-isopropylidene-3-hydroxy-4-hydroxymethyl-2-methyl)pyridylmethyl]-1,3-propanediol.

mp: 127°-128°

IR (KBr): 3380 cm$^{-1}$: OH; 1380 (doublet): (CH$_3$)$_2$C

Tosylation of the above diol (8.15 g, 31 mmol in 40 ml pyridine) by a solution of 12 g (63 mmol) tosyl chloride in 50 ml pyridine gave the corresponding ditosylate as a brown oil that was purified by column chromatography (8/2 CHCl$_3$/MeOH on SiO$_2$). An amount of 3.4 g (19% yield) was obtained.

IR (film): 1350 and 1170 cm$^{-1}$: SO$_2$

A solution of this ditosylate (2.7 g, 4.7 mmol) in 40 ml dioxane was reacted with a solution of sodium dibutyl phosphite (18.8 mmol in 40 ml tetrahydrofuran) in the usual manner. After removal of volatile compounds by ball-tube distillation, the residue was purified by column chromatography (95/5 CHCl$_3$/MeOH on SiO$_2$). Tetrabutyl 2-[5-(3,4-isopropylidene-3-hydroxy-4-hydroxymethyl-2-methyl)pyridyl methyl]-1,3-propylidenediphosphonate was obtained as a yellow oil (1.5 g, 52% yield).

IR (film): 2980 cm$^{-1}$: aliphatic C—H; 1380 (doublet): (CH$_3$)$_2$C; 1240: P=O; 1060-970: P—O—C MS: m/e=619 (M+)

NMR (CDCl$_3$): δ=7.82 (singlet, 1H): pyridyl $\underline{H}$; 4.87 (singlet, 3H): —CH$_2$—O$_2$—C(CH$_3$)$_2$—; 4.0 (multiplet, 8H): P—O—C$\underline{H}_2$CH$_2$CH$_2$CH$_3$; 2.76 (doublet, J=7 Hz, 2H): —C$\underline{H}_2$—CH—(CH$_2$PO$_3$Bu$_2$)$_2$; 2.40 (singlet, 3H): 2—CH$_3$—pyridine; 2.45-2.30 (multiplet, 1H): —C$\underline{H}$—(CH$_2$—PO$_3$Bu$_2$)$_2$; 2.10 (doublet of doublet of doublet, 2H): diastereotopic H$^a$: C($\underline{H}^a$)(H$^b$)—PO$_3$Bu$_2$; 1.84 (doublet of doublet of doublet, 2H): diastereotopic H$^b$: C(H$^a$)($\underline{H}^b$)—PO$_3$Bu$_2$; 1.70-1.60 (multiplet, 8H): P—O—CH$_2$C$\underline{H}_2$—CH$_2$—CH$_3$; 1.55 (singlet, 6H): isopropylidene $\underline{H}$; 1.44-1.34 (multiplet, 8H): P—O—CH$_2$—CH$_3$C$\underline{H}_2$CH$_3$; 0.95 (triplet, J=7 Hz, 12H): P—O—CH$_2$—CH$_2$—CH$_2$—C$\underline{H}_3$;

Deprotection of the isopropylidene derivative was carried out by warming to 55° the above compound (0.72 g, 1.16 mmol) in 13 ml 1N HCl. The reaction mixture was neutralized (pH 7-8) with saturated sodium bicarbonate and extracted into warm benzene. Purification by column chromatography (9:1 CHCl$_3$:MeOH on SiO$_2$) gave 0.2 g (30% yield) of tetrabutyl 2-[5-(3-hydroxy-4-hydroxymethyl-2-methylpyridylmethyl]-1,3-propylidenediphosphonate.

mp: 43°-44°

Elemental analysis C$_{27}$H$_{51}$NO$_8$P$_2$: Theor.: % C 55.95; % H 8.87; % P 10.68; Found: % C 55.87; % H 8.76; % P 10.49

IR (film): 3200 cm$^{-1}$: OH; 2980: C—H; 1230: P=O; 1040-970: P—O—C

NMR (CDCl$_3$): δ=7.75 (singlet, 1H): pyridyl $\underline{H}$; ca 5.85 (broad signal, exchange with D$_2$O) hydroxyl $\underline{H}$; 4.0-3.86 (multiplet, 8H): P—O—C$\underline{H}_2$'CH$_2$—CH$_2$—CH$_3$; 2.8 (doublet, J=7 Hz, 2H): —C$\underline{H}_2$—CH—(CH$_2$PO$_3$Bu$_2$)$_2$; 2.45 (singlet, 3H): 2—CH$_3$—pyridine; 2.50-2.35 (multiplet, 1H): —C$\underline{H}$—(C$\underline{H}_2$—PO$_3$Bu$_2$)$_2$; 2.0 (doublet of doublet of doublet, 2H): diastereotopic H$^a$: C($\underline{H}^a$)(H$^b$)—PO$_3$Bu$_2$; 1.76 (doublet of doublet of doublet, 2H): diastereotopic H$^b$: C(H$^a$)($\underline{H}^b$)—PO$_3$Bu$_2$; 2.65-2.55 (multiplet, 8H): P—O—CH$_2$—CHHD 2CH$_2$CH$_3$; 1.27 (splitted sextet, J=7 Hz, 8H): $\overline{P}$—O—CH$_2$—C$\underline{H}_2$CH$_2$CH$_3$; 0.94 (several triplets, J=7 Hz, 12H): P—O—CH$_2$—CH$_2$CH$_2$C$\underline{H}_3$

EXAMPLE 22

Tetrabutyl 2-[4-(4-phenylpiperazinylmethyl)benzyl]-1,3-propylidendiphosphonate

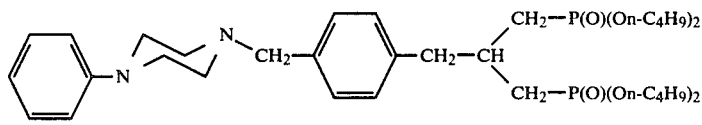

4-phenylpiperazine (41.4 g, 0.26 mol) was added to a solution of 4-(bromomethyl)benzonitrile (25 g, 0.13 mol) in 60 ml ethanol and the mixture was refluxed for one hour. After filtration of the precipitated N-phenylpiperazinium bromide, the filtrate was evaporated and the residue was recrystallized in a chloroform: acetone mixture to afford 28.6 g (79% yield) of 4-(4-phenylpiperazinylmethyl)benzonitrile.

mp: 154°–156°

IR (KBr): 2200 cm$^{-1}$: —CN

The above nitrile (28.0 g, 102 mmol) was dissolved in 150 ml of hot 1-propanol, 60 ml of a 10N sodium hydroxide solution were added and the resulting mixture was refluxed overnight. After cooling, the precipitate of sodium carboxylate was filtered, dissolved in 60 ml water and 60 ml 37% hydrochloric acid were added at 0°. The precipitate was filtered and dried under vacuum at 100°. An amount of 24 g (62% yield) of 4-(4-phenylpiperazinylmethyl)benzoic acid dihydrochloride was obtained.

mp: 250°–253° (dec)

IR (KBr): 3000–2500 and 1720 cm$^{-1}$: COOH

A suspension of lithium aluminum hydride (11.5 g, 303 mmol) in 240 ml tetrahydrofuran was added dropwise to a suspension of the above acid (24 g, 65 mmol) in the same solvent and the mixture was refluxed for 5 hours. After work-up, 12 g (65% yield) of 4-(4-phenylpiperazinylmethyl)benzyl alcohol were obtained.

mp: 109°–111°

IR (KBr): 3600 cm$^{-1}$: OH

Phosphorus tribromide (14.9 g, 55 mmol) was slowly introduced into a solution of the alcohol (12 g, 42 mmol) in 60 ml anhydrous benzene and the mixture was refluxed for 3 hours. Filtration yielded 16.6 g (92% yield) of crude 4-(4-phenylpiperazinylmethyl)benzyl bromide hydrobromide. This compound (16 g, 36 mmol) was reacted with a solution of 100 ml sodium diethyl malonate in ethanol (110 ml) at 60° for 5 hours. Ball-tube (Kugelrohr) distillation gave 5.3 g (35% yield) of diethyl 4-(4-phenylpiperazinylmethyl)benzyl malonate as a yellow oil that slowly crystallized.

bp: 210° (0.05 mm Hg)

IR (film): 1750 and 1730 cm$^{-1}$: C=O, 1130–1150 (C—O)

The above compound (5.0 g, 11.8 mmol) was reduced by a suspension of 0.58 g LiAlH$_4$ (15.4 mmol) in 60 ml dry tetrahydrofuran. Work-up gave 3.0 g (75% yield) of 2-[4-(4-phenylpiperazinylmethyl)benzyl]-1,3-propanediol.

mp: 135°–137° (acetone/ether)

IR (KBr): 3250 cm$^{-1}$ (OH), 1030 (C—O)

The above diol (3 g, 8.8 mmol) was reacted with tosylchloride (4.9 g, 26 mmol) in 20 ml pyridine to afford 4.3 g (75% yield) of ditosylate of 2-[4-(4-phenylpiperazinylmethyl)benzyl]-1,3-propanediol.

mp: 153°–154° (acetone)

IR (KBr): 1350 and 1170 cm$^{-1}$ (—SO$_2$—)

A solution of the above ditosylate (3.6 g, 5.6 mmol) in 10 ml dioxane was added to a solution of 23 mmol sodium dibutyl phosphite in 10 ml tetrahydrofuran and the resulting mixture was refluxed for 24 hours. After work-up, the residue was purified by column chromatography (adsorbent: —SiO$_2$, eluent: 99/1 CHCl$_3$/MeOH) to afford 1.5 g (39% yield) of a white oil of tetrabutyl 2-[4-(4-phenylpiperazinylmethyl)benzyl]-1,3-propylidenediphosphonate.

IR (film): 2960 cm$^{-1}$: aliphatic C—H; 1600: aromatic C—C; 1240: P=O; 1060–970: P—O—C; 690+750: aromatic H NMR (CDCl$_3$): δ=7.35–7.18 and 6.90–6.85 (total: 9H): Aromatic H; 4.1–3.96 (multiplet, 8H): P—O—CH$_2$—CH$_2$—CH$_2$—CH$_3$; 3.56 (singlet, 2H): C$_4$H$_8$N$_2$—CH$_2$; 3.25 and 2.65: (two distorted triplets, 8H): C$_4$H$_8$N$_2$; 2.93 (doublet, 7 Hz, 2H): CH$_2$—CH(CH$_2$PO$_3$)$_2$; 2.60–2.45 (multiplet, 1H): —CH—(CH$_2$PO$_3$)$_2$; 2.08 (doublet of doublet of doublet, 2H): diastereotopic H$^a$: C(H$^a$)(H$^b$)PO$_3$Bu$_2$; 1.88 (doublet of doublet of doublet, 2H): diastereotopic H$^b$: C(H$^a$)(H$^b$)—PO$_3$Bu$_2$; 1.70–1.60 (multiplet, 8H): P—O—CH$_2$CH$_2$CH$_2$CH$_3$; 1.44 (sextet, 8H): P—O—CH$_2$CH$_2$CH$_2$—CH$_3$; 0.98 (triplet, 12H): P—O—CH$_2$CH$_2$CH$_2$CH$_3$

EXAMPLE 23

Tetrabutyl 2-[3-(2-methyl-1,3-dioxolane-2-yl)propyl]-1,3-propylidenediphosphonate

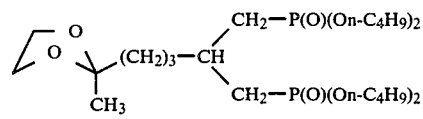

2-(3-chloropropyl)-2-methyl-1,3-dioxolane (27 g, 0.164 mol) was reacted overnight at reflux temperature with an equimolar amount of sodium diethyl malonate in 100 ml absolute ethanol. Ball-tube distillation gave 22 g (47%) of diethyl 3-(2-methyl-1,3-dioxolane-2-yl)propyl malonate.

bp: 140° (0.05 mm Hg)

IR (film): 1740 cm$^{-1}$ (C=O), 1200 (C—O)

A solution of the above compound (22 g, 76 mmol in 30 ml diethylether) was added to a suspension of 3.8 g (100 mmol) LiAlH$_4$ in 150 ml diethylether and the resulting mixture was stirred at room temperature for 4 hours. A 10% NaOH solution was added to destroy the excess of hydride and the ether solution is decanted from the hydroxides. After evaporation of the ether phase, ball-tube distillation of the residue afforded 4 g (26% yield) of 2-[3-(2-methyl-1,3-dioxolane-2-yl)propyl]-1,3-propanediol.

bp: 105°–120° (0.05 mm Hg)

IR (film): 3400 cm$^{-1}$ (OH), 1030+1050: C—O.

Tosylation by the standard procedure (tosyl chloride in pyridine) gave 7 g (70% yield) of ditosylate of 2-[3-(2- methyl-1,3-dioxolane-2-yl)propyl]-1,3-propanediol as a viscous oil.

IR (film): 1360, 1190+1170 cm$^{-1}$: —SO$_2$—

A solution of the above ditosylate (4 g, 7.8 mmol) in 15 ml dioxane was reacted with a solution of 20 mmol sodium dibutyl phosphite in 15 ml tetrahydrofuran at reflux temperature for 16 hours. Ball-tube fractionation gave 1.8 g (41% yield) of tetrabutyl 2-[3-(2-methyl-1,3-dioxolane-2-yl)propyl]-1,3-propylidenediphosphonate.

bp: 200° (0.05 mm Hg)

IR (film): 2980 cm$^{-1}$: aliphatic C—H; 1240: P=O; 970, 1030, 1050: P—O—C

NMR (CDCl$_3$) δ=4.08-3.96 (multiplet, 8H): P—O—C$\underline{H}_2$—CH$_2$—CH$_2$—CH$_3$; 3.96-3.90 (multiplet, 4H): C$_2$$\underline{H}_4$O$_2$—(CH$_3$); 2.33-2.14 (multiplet, 1H): —C$\underline{H}$—(CH$_2$PO$_3$Bu$_2$)$_2$; 2.14-1.96 (multiplet, 4H): diastereotopic H$^a$: C($\underline{H}^a$)(H$^b$)—PO$_3$Bu$_2$+C$_2$H$_4$O$_2$(CH$_3$)—C$\underline{H}_2$—; 1.86 (distorted doublet of doublet of doublet, 2H): diastereotopic H$^b$ C(H$^a$)($\underline{H}^b$)—PO$_3$Bu$_2$; 1.65 (partially overlapped quintet, 12H): —(C$\underline{H}_2$)$_2$—CH(CH$_2$PO$_3$Bu$_2$)$_2$+P—O—CH$_2$—CH$_2$—C$\underline{H}_2$—CH$_3$; 1.42 (sextet, 8H); P—O—CH$_2$CH$_2$C$\underline{H}_2$CH$_3$; 1.33 (singlet, 3H): C$_2$H$_4$O$_2$(C$\underline{H}_3$)—; 0.95 (triplet, 12H): P—O—CH$_2$—CH$_2$—CH$_2$—C$\underline{H}_3$

EXAMPLE 24

Tetraethyl 2-(5-phenyl-1,3-dioxane-2-yl-methyl)-1,3-propylidenediphosphonate

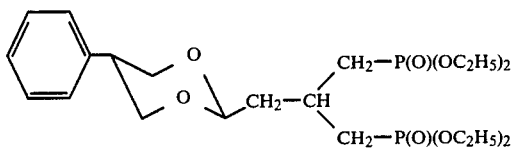

Following the procedure described by Bedoukian (Journal of American Chemical Society, Vol. 66, p. 651, 1944) 2-bromomethyl-5-phenyl-1,3-dioxane was synthesized by reacting 1,2-dibromomethyl acetate (obtained by reacting vinyl acetate with bromine in carbon tetrachloride) with 2-phenyl-1,3-propanediol (obtained by reduction of diethyl phenyl malonate with LiAlH$_4$).

2-bromomethyl-5-phenyl-1,3-dioxane was condensed with diethyl malonate to give the corresponding substituted malonate that was reduced to 2-(5-phenyl-1,3-dioxane-2-yl-methyl)-1,3-propanediol by LiAlH$_4$ in diethyl ether such as described in example 23. Tosylation was carried out by the usual tosyl chloride/pyridine procedure.

A solution of the ditosylate of 2-(5-phenyl-1,3-dioxane-2-yl-methyl)-1,3-propanediol (4.5 g, 80 mmol) in 20 ml dioxane was reacted at room temperature for 15 hours with a solution of 20 mmol sodium diethyl phosphite in 20 ml tetrahydrofuran. Ball-tube distillation followed by column chromatography (95/5 CHCl$_3$/MeOH on SiO$_2$) gave 2.0 g (50% yield) of tetraethyl 2-(5-phenyl-1,3-dioxane-2-yl-methyl)-1,3-propylidenephosphonate.

IR: 2980 cm$^{-1}$: aliphatic C—H; 1240: P=O; 1165: P—O—Et; 1040: P—O—C; 790: aromatic C—H General Properties of 1,3-Diphosphonates (I)

$$A-CH \begin{matrix} CH_2-P(O)(OR^1)(OR^2) \\ CH_2-P(O)(OR^1)(OR^2) \end{matrix} \quad (I)$$

| Compounds | A | $R^1, R^2$ | mp(°C.) | bp(°C./mm Hg) | IR absorptions (cm$^{-1}$) |
|---|---|---|---|---|---|
| 1 | C$_6$H$_5$— | H | 153–155 | | 2900 + 2300 (broad): P—OH |
| 2 | C$_6$H$_5$—CH$_2$— | H | 158–160 | | 1500: aromatic C—C |
| 3 | C$_6$H$_5$—(CH$_2$)$_2$— | H | 142–145 | | 1200 + 1130: P=O |
| 4 | C$_6$H$_5$—(CH$_2$)$_3$— | H | 124–126 | | 1000 + 950: P—OH |
| 5 | 4-Cl-C$_6$H$_4$—CH$_2$— | H | 164–167 | | 750: aromatic C—H |
| 6 | C$_6$H$_5$—O—(CH$_2$)$_2$— | H | 149–153 | | |
| 7 | n-C$_5$H$_{11}$— | CH$_3$ | | 140–145/0.05 | |
| 8 | cyclohexyl-CH$_2$— | CH$_3$ | | 155–160/0.05 | |

-continued

General Properties of 1,3-Diphosphonates (I)

$$A-CH\begin{pmatrix}CH_2-P(O)(OR^1)(OR^2)\\CH_2-P(O)(OR^1)(OR^2)\end{pmatrix} \quad (I)$$

| No. | A | OR¹/OR² | bp (°C/mmHg) | IR |
|---|---|---|---|---|
| 9 | cyclohexyl–(CH₂)₃– | CH₃ | 160–165/0.05 | |
| 10 | C₆H₅–CH₂– | CH₃ | 150–152/0.05 | 2980: aliphatic C—H |
| 11 | C₆H₅–(CH₂)₂– | CH₃ | 150–155/0.05 | 1240: P=O |
| 12 | C₆H₅–(CH₂)₃– | CH₃ | 155–160/0.05 | 1195: P—O—CH₃ |
| 13 | C₆H₅–O–(CH₂)₂– | CH₃ | 170–175/0.05 | 1030: P—O—C |
| 14 | C₆H₅–O–(CH₂)₃– | CH₃ | 172–175/0.05 | |
| 15 | n-C₅H₁₁– | C₂H₅ | 145–150/0.05 | |
| 16 | n-C₁₄H₂₉– | C₂H₅ | 215–220/0.05 | |
| 17 | n-C₁₆H₃₃– | C₂H₅ | 220–225/0.05 | |
| 18 | cyclohexyl– | C₂H₅ | 150–155/0.05 | 2980: aliphatic C—H<br>1240: P=O |
| 19 | cyclohexyl–CH₂– | C₂H₅ | 160–165/0.05 | 1160: P—O—C₂H₅ |

-continued

General Properties of 1,3-Diphosphonates (I)

$$A-CH\begin{matrix}CH_2-P(O)(OR^1)(OR^2)\\CH_2-P(O)(OR^1)(OR^2)\end{matrix}\quad (I)$$

| No. | A | R¹, R² | bp (°C/mmHg) | IR (cm⁻¹) |
|---|---|---|---|---|
| 20 | cyclohexyl-(CH₂)₃— | C₂H₅ | 168–170/0.05 | 1030: P—O—C |
| 21 | piperidinyl-N—(CH₂)₂— | C₂H₅ | 157–160/0.05 | |
| 22 | piperidinyl-N—(CH₂)₂— | C₂H₅ | 160–165/0.05 | |
| 23 | morpholinyl-N—(CH₂)₂— | C₂H₅ | 162–165/0.05 | |
| 24 | phenyl— | C₂H₅ | 148–152/0.05 | 2980: aliphatic C—H |
| 25 | phenyl-CH₂— | C₂H₅ | 153–155/0.05 | 1240 P=O |
| 26 | phenyl-(CH₂)₂— | C₂H₅ | 157–162/0.05 | 1160: P—O—C₂H₅ |
| 27 | phenyl-(CH₂)₃— | C₂H₅ | 160–165/0.05 | 1030: P—O—C |

-continued

General Properties of 1,3-Diphosphonates (I)

$$A-CH \begin{matrix} CH_2-P(O)(OR^1)(OR^2) \\ CH_2-P(O)(OR^1)(OR^2) \end{matrix} \quad (I)$$

| No. | A | R¹ = R² | bp (°C/mmHg) | IR (cm⁻¹) |
|---|---|---|---|---|
| 28 | 2-methylbenzyl (–CH₂–C₆H₄–CH₃, o) | C₂H₅ | 155–160/0.05 | 2980: aliphatic C—H |
| 29 | 4-fluorobenzyl (–CH₂–C₆H₄–F, p) | C₂H₅ | 160–162/0.05 | 1240: P=O |
| 30 | 4-chlorobenzyl (–CH₂–C₆H₄–Cl, p) | C₂H₅ | 165–170/0.05 | 1160: P—O—C₂H₅ |
| 31 | 2,5-dimethylphenoxyethyl (CH₃-substituted –O–(CH₂)₂–) | C₂H₅ | 190–195/0.05 | 1030: P—O—C |
| 32 | –(CH₂)₂–O–(CH₂)₂–phenyl | C₂H₅ | 190–195/0.05 | 790: aromatic C—H |
| 33 | phenoxyethyl (–O–(CH₂)₂–C₆H₅) | C₂H₅ | 180–182/0.05 | 2980: aliphatic C—H |
| 34 | phenoxypropyl (–O–(CH₂)₃–C₆H₅) | C₂H₅ | 185–190/0.05 | 1240: P=O |

-continued
General Properties of 1,3-Diphosphonates (I)
$$A-CH\begin{matrix}CH_2-P(O)(OR^1)(OR^2)\\CH_2-P(O)(OR^1)(OR^2)\end{matrix} \quad (I)$$
| | A | | |
|---|---|---|---|
| 35 | –O–(CH$_2$)$_4$–phenyl | C$_2$H$_5$ | 190–195/0.05 | 1160: P—O—C$_2$H$_5$ |
| 36 | 3,4,5-tri(CH$_3$O)–C$_6$H$_2$–CH$_2$– | C$_2$H$_5$ | 195–200/0.05 | 1030: P—O—C |
| 37 | 1-naphthyl–CH$_2$– | C$_2$H$_5$ | 195–200/0.05 | 790: aromatic C—H |
| 38 | 4-biphenyl–CH$_2$– | C$_2$H$_5$ | 210–215/0.05 | 2980: aliphatic C—H |
| 39 | diphenyl–CH– | C$_2$H$_5$ | 190–195/0.05 | 1240: P=O |
| 40 | 2-pyridyl | C$_2$H$_5$ | 150–155/0.05 | 1160: P—O—C$_2$H$_5$ |

-continued
General Properties of 1,3-Diphosphonates (I)

$$A-CH\begin{array}{c}CH_2-P(O)(OR^1)(OR^2)\\CH_2-P(O)(OR^1)(OR^2)\end{array} \quad (I)$$

| | A— | OR¹, OR² | m.p./mmHg | IR (cm⁻¹) |
|---|---|---|---|---|
| 41 | 4-pyridyl-CH₂— | C₂H₅ | * | 1030: P—O—C |
| 42 | 3-pyridyl-(CH₂)₃— | C₂H₅ | * | 790: aromatic C—H |
| 43 | 4-Br-C₆H₄—O—(CH₂)₂— | C₂H₅ | 190–195/0.05 | 2980: aliphatic C—H |
| 44 | 4-C₆H₅-C₆H₄—O—(CH₂)₂— | C₂H₅ | 185–190/0.05 | 1240: P=O |
| 45 | 3,5-(CH₃)₃C-4-HO-C₆H₂—CH₂— | C₂H₅ | 195–200/0.05 | 1160: P—O—C₂H₅ |
| 46 | C₆H₅—N(CH₂CH₂—)N—C₆H₄—CH₂— | C₂H₅ | ** | 1030: P—O—C |

-continued
General Properties of 1,3-Diphosphonates (I)

$$A-CH\begin{matrix}CH_2-P(O)(OR^1)(OR^2)\\CH_2-P(O)(OR^1)(OR^2)\end{matrix} \quad (I)$$

| No. | A | R¹ | R² | bp (°C/mmHg) | IR (cm⁻¹) |
|---|---|---|---|---|---|
| 47 | phenyl-CH₂-O-CH₂-CH(-O-)CH₂- (1,3-dioxolane with benzyl) | C₂H₅ | C₂H₅ | ** | 790: aromatic C—H |
| 48 | cyclohexyl-(CH₂)₃- | n-C₃H₇ | n-C₃H₇ | 180–185/0.05 | |
| 49 | phenyl-CH₂- | n-C₃H₇ | n-C₃H₇ | 170–175/0.05 | |
| 50 | phenyl-(CH₂)₃- | n-C₃H₇ | n-C₃H₇ | 175–180/0.05 | 2980: aliphatic C—H |
| 51 | 2,5-dimethylphenyl-O-(CH₂)₂- | n-C₃H₇ | n-C₃H₇ | 205–210/0.05 | 1240: P=O |
| 52 | phenyl-O-(CH₂)₂- | n-C₃H₇ | n-C₃H₇ | 195–200/0.05 | 1000: P—O—C |
| 53 | phenyl-O-(CH₂)₃- | n-C₃H₇ | n-C₃H₇ | 197–202/0.05 | |
| 54 | cyclohexyl-(CH₂)₃- | i-C₃H₇ | i-C₃H₇ | 170–175/0.05 | |

-continued

General Properties of 1,3-Diphosphonates (I)

$$A-CH\begin{matrix}CH_2-P(O)(OR^1)(OR^2)\\CH_2-P(O)(OR^1)(OR^2)\end{matrix}\quad (I)$$

| # | A | OR¹/OR² | bp | IR |
|---|---|---|---|---|
| 55 | C₆H₅—CH₂— | i-C₃H₇ | 160–165/0.05 | 2980: aliphatic C—H |
| 56 | C₆H₅—(CH₂)₃— | i-C₃H₇ | 165–170/0.05 | 1390 + 1385: isopropyl |
| 57 | C₆H₅—O—(CH₂)₂— | i-C₃H₇ | 185–188/0.05 | 1240: P=O |
| 58 | C₆H₅—O—(CH₂)₃— | i-C₃H₇ | 185–190/0.05 | 990: P—O—C |
| 59 | 1-naphthyl-CH₂— | i-C₃H₇ | 200–205/0.05 | 750: aromatic C—C |
| 66 | n-C₅H₁₁— | n-C₄H₉ | 175–180/0.05 | |
| 67 | (CH₃)₂CH—CH₂— | n-C₄H₉ | 175–180/0.05 | |
| 68 | cyclohexyl-(CH₂)₃— | n-C₄H₉ | 190–195/0.05 | 2980: aliphatic C—H |

-continued
General Properties of 1,3-Diphosphonates (I)

$$A-CH\begin{matrix}CH_2-P(O)(OR^1)(OR^2)\\CH_2-P(O)(OR^1)(OR^2)\end{matrix} \quad (I)$$

| No. | A | R¹, R² | b.p. (°C/mbar) | IR (cm⁻¹) |
|---|---|---|---|---|
| 69 | ![pyrrolidine-N-(CH₂)₂-] | n-C₄H₉ | * | 1240: P=O |
| 70 | ![piperidine-N-(CH₂)₂-] | n-C₄H₉ | * | 1070-980: P—O—C |
| 71 | ![morpholine-N-(CH₂)₂-] | n-C₄H₉ | * | |
| 72 | 4-Cl-C₆H₄-CH₂- | n-C₄H₉ | 185-190/0.05 | |
| 73 | C₆H₅-CH₂- | n-C₄H₉ | 175-180/0.05 | |
| 74 | C₆H₅-(CH₂)₂- | n-C₄H₉ | 182-185/0.05 | 2980: aliphatic C—H |
| 75 | C₆H₅-(CH₂)₃- | n-C₄H₉ | 185-190/0.05 | 1240: P=O |
| 76 | C₆H₅-C(CH₃)₂-CH₂- | n-C₄H₉ | 185-190/0.05 | 1070-980: P—O—C |

-continued

General Properties of 1,3-Diphosphonates (I)

$$A-CH\begin{cases}CH_2-P(O)(OR^1)(OR^2)\\CH_2-P(O)(OR^1)(OR^2)\end{cases} \quad (I)$$

| | A | R¹ = R² | b.p. (°C/mbar) | IR (cm⁻¹) |
|---|---|---|---|---|
| 77 | 2,5-dimethylphenyl-O-(CH₂)₂- | n-C₄H₉ | 215–220/0.05 | 750: aromatic C—C |
| 78 | 4-chloro-2-methylphenyl-O-(CH₂)₂- | n-C₄H₉ | 220–225/0.05 | |
| 79 | phenyl-O-(CH₂)₂- | n-C₄H₉ | 205–210/0.05 | |
| 80 | phenyl-O-(CH₂)₃- | n-C₄H₉ | 210–215/0.05 | 2980: aliphatic C—H |
| 81 | phenyl-O-(CH₂)₄- | n-C₄H₉ | 215–220/0.05 | 1240: P=O |
| 82 | 3,4,5-trimethoxyphenyl-CH₂- | n-C₄H₉ | 218–220/0.05 | 1070–980: P—O—C |

-continued
General Properties of 1,3-Diphosphonates (I)

$$A-CH \begin{matrix} CH_2-P(O)(OR^1)(OR^2) \\ CH_2-P(O)(OR^1)(OR^2) \end{matrix} \quad (I)$$

| No. | A | R¹, R² | b.p. (°C/mmHg) | IR (cm⁻¹) |
|---|---|---|---|---|
| 83 | 1-naphthyl-CH₂– | n-C₄H₉ | 220–225/0.05 | 750: aromatic C—C |
| 84 | 4-biphenyl-CH₂– | n-C₄H₉ | 235–240/0.05 | |
| 85 | (C₆H₅)₂CH– | n-C₄H₉ | 210–220/0.05 | 2980: aliphatic C—H |
| 86 | 2-pyridyl-CH₃ (2-methylpyridine) | n-C₄H₉ | 170–175/0.05 | 1240: P=O |
| 87 | 4-pyridyl-CH₂– | n-C₄H₉ | * | 1070–980: P—O—C |
| 88 | 3-pyridyl-(CH₂)₃– | n-C₄H₉ | * | 750: aromatic C—C |

-continued

General Properties of 1,3-Diphosphonates (I)

$$A-CH{\overset{CH_2-P(O)(OR^1)(OR^2)}{\underset{CH_2-P(O)(OR^1)(OR^2)}{}}} \quad (I)$$

| | A | R¹=R² | |
|---|---|---|---|
| 89 | 4-F-C₆H₄-O-(CH₂)₂- | n-C₄H₉ | 210-215/0.05 |
| 90 | 4-Cl-C₆H₄-O-(CH₂)₂- | n-C₄H₉ | 215-220/0.05  2980: aliphatic C—H |
| 91 | 4-Br-C₆H₄-O-(CH₂)₂- | n-C₄H₉ | 220-225/0.05  1240: P=O |
| 92 | 4-CH₃O-C₆H₄-O-(CH₂)₂- | n-C₄H₉ | 218-220/0.05  1070-980: P—O—C |
| 93 | 3-CF₃-C₆H₄-O-(CH₂)₂- | n-C₄H₉ | 210-215/0.05  750: aromatic C—C |
| 94 | 4-n-C₃H₇-O-C₆H₄-O-(CH₂)₂- | n-C₄H₉ | 220-225/0.05 |
| 95 | 2,6-Cl₂-C₆H₃-O-(CH₂)₂- | n-C₄H₉ | 220-225/0.05 |

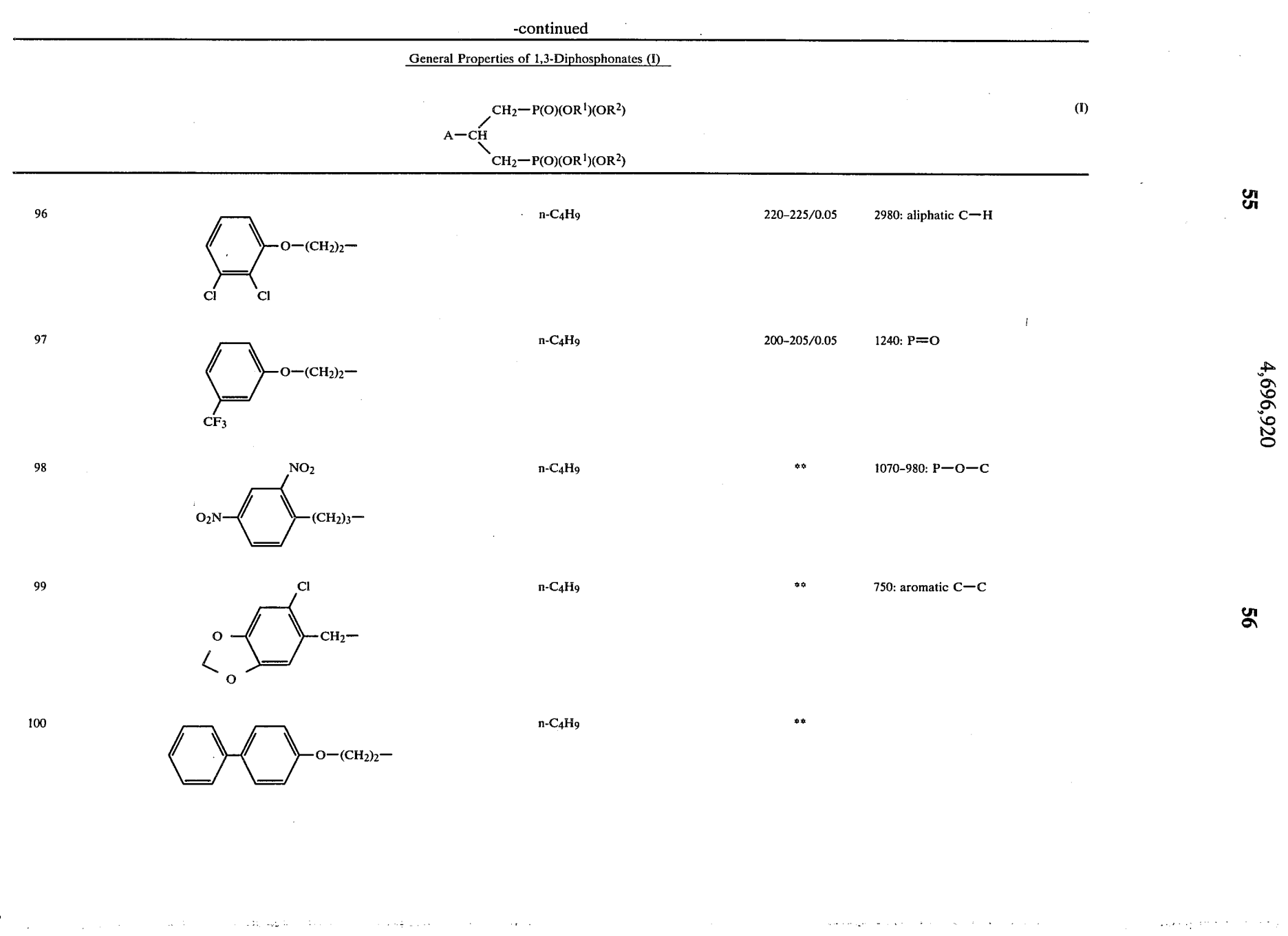

-continued

General Properties of 1,3-Diphosphonates (I)

$$A-CH\begin{matrix}CH_2-P(O)(OR^1)(OR^2)\\ CH_2-P(O)(OR^1)(OR^2)\end{matrix} \quad (I)$$

| No. | A | R¹=R² | bp/mp | IR |
|---|---|---|---|---|
| 96 | 2,3-dichlorophenyl-O-(CH₂)₂- | n-C₄H₉ | 220–225/0.05 | 2980: aliphatic C—H |
| 97 | 3-CF₃-phenyl-O-(CH₂)₂- | n-C₄H₉ | 200–205/0.05 | 1240: P=O |
| 98 | 2-NO₂-4-NO₂-phenyl-(CH₂)₃- | n-C₄H₉ | ** | 1070–980: P—O—C |
| 99 | (methylenedioxy-Cl-phenyl)-CH₂- | n-C₄H₉ | ** | 750: aromatic C—C |
| 100 | 4-biphenyl-O-(CH₂)₂- | n-C₄H₉ | ** | |

4,696,920

-continued
General Properties of 1,3-Diphosphonates (I)

$$A-CH\begin{matrix}CH_2-P(O)(OR^1)(OR^2)\\CH_2-P(O)(OR^1)(OR^2)\end{matrix} \quad (I)$$

| # | A | R¹, R² | m.p. (°C) | b.p. (°C/mbar) | IR (cm⁻¹) |
|---|---|---|---|---|---|
| 101 | 3-methoxy-(2-methyl-5-methyl-pyridin-4-yl)methyl (isopropylidene-protected) | n-C₄H₉ | | ** | 2980: aliphatic C—H |
| 102 | (3-hydroxy-2-methyl-5-hydroxymethyl-pyridin-4-yl)methyl | n-C₄H₉ | 43–44 | ** | 1240: P=O |
| 103 | 4-[(2-(N-methyl-N-aminoethyl)amino)methyl]benzyl | n-C₄H₉ | | ** | 1070–980: P—O—C |
| 104 | 4-[(2-(N-phenylamino)ethyl)amino)methyl]benzyl | n-C₄H₉ | | ** | 750: aromatic C—C |
| 105 | 4-[(N-methyl-N-phenylamino)methyl]benzyl | n-C₄H₉ | | ** | |
| 106 | 3-(2,2-dimethyl-1,3-dioxolan-4-yl)propyl | n-C₄H₉ | | 200/0.05 | 2980: aliphatic C—H |

-continued
General Properties of 1,3-Diphosphonates (I)
$$A-CH\begin{array}{c}CH_2-P(O)(OR^1)(OR^2)\\CH_2-P(O)(OR^1)(OR^2)\end{array} \quad (I)$$
| | A | R¹, R² | bp (°C/mmHg) | IR (cm⁻¹) |
|---|---|---|---|---|
| 107 |  | n-C₄H₉ | 200/0.05 | 1240: P=O |
| 108 | (benzyl-dioxane) | n-C₄H₉ | ** | 1070–980: P—O—C |
| 109 | (pyridyl-dioxane) | n-C₄H₉ | ** | |
| 110 | PhO—(CH₂)₂— | —CH₂—CH₂—CH=CH₂ | 205–210/0.05 | 3080–1630(CH=CH₂), 1230, 1030 |
| 111 | Ph—(CH₂)₃— | i-C₄H₉ | 180–185/0.05 | 2980, 1400 + 1370, 1240, 1020 |
| 112 | Ph—(CH₂)₃— | n-C₅H₁₁ | 210–215/0.05 | 2980, 1240, 1050–990 |
| 113 | Ph—(CH₂)₃— | n-C₆H₁₃ | 225–230/0.05 | 2960, 1240, 1050–1000 |

-continued
General Properties of 1,3-Diphosphonates (I)

$$A-CH\begin{matrix}CH_2-P(O)(OR^1)(OR^2)\\CH_2-P(O)(OR^1)(OR^2)\end{matrix} \quad (I)$$

| Cpds | A | R¹ | R² | bp(°C./mm Hg) | IR absorptions (cm$^{-1}$) |
|------|---|----|----|---------------|----------------------------|
| 114 | C₆H₅—CH₂— | — | CH₂CH₂N(CH₃)₂ | — | 2970, 2820 + 2770, 1240, 1030–950 |
| 115 | C₆H₅—CH₂— | — | cyclohexyl-CH₂ | * | 2970, 1260, 980 |
| 116 | C₆H₅—CH₂— | C₂H₅ | n-C₅H₁₁ | 186–190/0.05 | 2960: aliphatic C—H |
| 117 | C₆H₅—(CH₂)₃— | C₂H₅ | n-C₅H₁₁ | 195–200/0.05 | 1240: P=O<br>1020: P—O—C |
| 118 | C₆H₅—CH₂— | CH₃ | H | — | 2900 + 2300, 1600, 1240, 1030 |
| 119 | C₆H₅—(CH₂)₃— | C₂H₅ | C₄H₉ | 195–200/0.05 | 2980, 1240, 1030–980 |
| 120 | C₆H₅—(CH₂)₃— | C₄H₉ | H | — | 2900 + 2300, 1240, 1030 |

*Purified by column chromatography (9/1 CHCl₃/MeOH)
**Purified by column chromatography (99/1–9/1 CHCl₃/MeOH)

The 1,3-diphosphonates previously described were tested in our routine pharmacological screening protocols and were found unexpectedly to display marked cardiovascular activity.

For this reason compounds from a broad series of 1,3-diphosphonates were studied in a secondary screening program to specifically determine their activity in:

Modulating [$^3$H]-Nitrendipine binding to brain membranes

Inhibiting KCl induced rat trachea contraction

Altering the isolated atrium rate

Producing hypotensive activity in rats

Results from these studies (described in this patent application) proved that 1,3-diphosphonates are in fact "calcium antagonists" and that they display potent pharmacological activity by their ability to affect the excitability of contractile cells. Compounds from this specific class alter the activity of the slow calcium channel of eukaryotic cell membranes and have been shown to be useful in the treatment of numerous diseases produced by or associated with dysfunctions of such channels, i.e. heart diseases, hypertension, angina pectoris, arrhythmias, asthma and gastrointestinal motility.

The structural formula (I) representing the 1,3-diphosphonate compounds which display calcium antagonist activity is chemically unrelated to any of the general formulas of the four classes of calcium antagonists developed to date:

Dihydropyridines: Nifedipine, Nitrendipine, Nimodipine etc . . . .

Benzothiazepine: Diltiazem, KB-944 (Fostedil)

Verapamil-type: Gallopamil, Verapamil, Anipamil, Tiapamil etc . . . .

Phenyl Alkylamine: Prenylamine, Fendiline

To our knowledge this is the first report of 1,3-diphosphonates esters demonstrating calcium antagonist activity due to inhibition of the calcium slow channel.

I. Potential uses of 1,3-diphosphonates

The present invention relates to the discovery that 1,3-diphosphonates of formula I are specific modulators (inhibitors and stimulators) of the calcium channel binding site for [$^3$H]-Nitrendipine. The modulating activity of this new class of Ca$^{++}$ antagonists encompasses the spectrum covered to date by chemically unrelated drugs which are known to be either stimulators (Diltiazem) or inhibitors (Verapamil). Biological and pharmacological tests performed in vitro and in vivo confirmed that these 1,3-diphosphonates are Ca$^{++}$ channel antagonists and are therefore potentially useful in the treatment of diseases such as:

angina: vasospastic, unstable at rest, and chronic stable, supra ventricular tachycardia, ventricular tachyarrythmia, atrial flutter and fibrillation, hypertension, cerebral insufficiency and vasospasm, pulmonary hypertension, asthma, premature labor, primary dysmenorrhea, myometrial hyperactivity, myocardiac ischemia and failure, cardiac preservation, intestinal spasm, peripheral vascular disease, oesophagal motor disorder, achalasia, hypersecretion of cellular products due to the release of materials stored in granules and secreted through a calcium dependent process, and platelet hyperaggregability.

It should also be noted that various pharmacological activities such as antihistaminic, neuroleptic, antischizophrenic and anticholinergic effects, were recently found to be associated with a Ca$^{++}$ channel inhibitory activity as well as a modulation of the [$^3$H]-Nitrendipine binding site (see Murphy et al Proc. Nat. Acad. Sci. 80, 860, 1983). Since most Ca$^{++}$ antagonists are amphiphilic chemicals they are known to interact with other membrane bound proteins, to display local anesthetic activities, and to inhibit various membrane-bound enzymes such as Na$^+$/K$^+$ ATPase, ACAT, adenylate cyclase, phospholipases, etc. Thus such activities might also be displayed by 1,3-diphosphonates of formula (I).

II. Mechanism of action of calcium antagonists and rationale for the screening protocols used in this application It is generally well accepted that fluctuations of the free Ca$^{++}$ level within cells regulate several processes such as muscle contraction and secretory functions (Kretsinger, R. H. Adv. Cycl. Nuc. Res. 11, 1–26, 1979). Calcium specific entry, exit and sequestration processes exist within the plasma membrane and intracellular organelles. These processes function both to generate the elevated level of Ca$^{++}$ during excitation and to restore and maintain the low intracellular Ca$^{++}$ levels of the resting state.

In principle, Ca$^{++}$ mobilization during cellular contraction may be initiated from both intracellular and extracellular sources, the extent of which will depend on several factors. The first class of drugs which were able to decrease the effect of calcium ion on cellular functions such as muscle contraction was discovered and named calcium antagonists (Fleckenstein, A. Pfluegers Arch. 307, R25, 1969). Classical examples of these drugs: Nifedipine, Verapamil and Diltiazem were shown to inhibit with very high specificity the slow inward current of the action potential.

(a) Effect of Ca$^{++}$ channel inhibition on cardiac electrical activity

The heart rate is controlled and triggered by pacemaker cells, atrio-ventricular sinus and nodal cells. Because of their dependence on calcium, pacemakers are very sensitive to calcium blocking drugs. In these cells calcium is thought to:

be in part responsible for generation of pacemaker potentials, be responsible for the conduction of the signal, carry in part the current responsible for the plateau and the overshoot phases, and stabilize cardiac membranes and suppress pacing activity in the Purkinje fibers.

All Ca$^{++}$ channel inhibitory drugs have been demonstrated to exert potent negative inotropic and chronotropic (decrease heart rate) effects on isolated atrium preparations. As a screening model the applicants have studied the chronotropic effect of 1,3-diphosphonates on isolated rat atrium.

(b) Effect of Ca++ channel inhibition on smooth muscle cells

The ability of Ca++ blocking drugs to interfere with the function of contractile tissues is displayed to the greatest extent on vascular smooth muscle and visceral smooth muscle (musculature of trachea, intestine, uterus and ureters). The hemodynamic result of Ca++ channel blockade in vascular smooth muscle is vasodilation leading in some cases to hypotension. The activity of calcium blockers in arteriolar smooth muscle is most marked in the coronary arteries where they produce profound vasodilation.

The inhibitory effect of 1,3-diphosphonates on contraction of smooth muscle cells (trachea) as well as their hypotensive activity were quantitated using the appropriate tests.

(c) Binding of calcium channel inhibitors to membrane receptors

Recently (1983) several authors have shown that the Ca++ channel receptor site can be labeled using [$^3$H]-Nitrendipine (Gould, R. J. et al Proc. Nat. Acad. Sci. 79, 3656, 1982; Bellemann, P. et al Proc. Nat. Acad. Sci. 80, 2356, 1983). These authors and Murphy K. M. M. et al (Proc. Nat. Acad. Sci. 80, 860, 1983) have shown that the modulation of [$^3$H]-Nitrendipine binding to its receptor(s) can be used to predict Ca++ antagonist activity for a wide array of compounds.

[$^3$]-Nitrendipine binding to drug receptor sites associated with calcium channels is allosterically regulated by various groups of Ca++ channel antagonists. Verapamil, D-600, Tiapamil, Lidoflazine, Flunarizine, Cinnarizine and Prenylamine all reduce [$^3$H]-Nitrendipine binding affinity, in contrast Diltiazem enhances [$^3$H]Nitrendipine binding.

The applicants used this radioreceptor assay to prove that the class of 1,3-diphosphonates are modulators of [$^3$H]-Nitrendipine binding, since this new assay for calcium antagonists has the advantage of being highly reproducible and specific for this class of drugs.

A. MODULATION OF [$^3$H]-NITRENDIPINE BINDING TO BRAIN MEMBRANES BY 1,3 DIPHOSPHONATES (a) Materials

[$^3$]-Nitrendipine (70 Ci/mmol, 1 Ci=3.7-10$^{10}$ Bq), Flunarizine, Prenylamine lactate, Nifedipine, TMB-8 and Verapamil were obtained commercially. Diltiazem hydrochloride was a generous gift from Goedecke A. G.

Water insoluble compounds were dissolved in absolute ethanol to give 10 mM or 2.5 mM stock solutions. Suitable dilutions were made in 50 mM Tris-HCl buffer (pH 7.4) containing 150 mM NaCl and 1 mM CaCl$_2$. The ethanol concentration in the final assay never exceeded 0.1%.

The purity of the radioligand and of the various agents tested was monitored by thin layer chromatography on silica gel plates.

(b) Methods

The following procedure was adapted from Bellemann et al (Proc. Nat. Acad. Sci. 80, 2356, 1983), and Gould et al (Proc. Nat. Acad. Sci. 79, 3656, 1982).

Adult male Wistar rats weighing 250–300 g were anesthetized with carbon dioxide prior to decapitation. The brain was removed then immersed in ice-cold 0.32M sucrose and washed 2–3 times with fresh solution. Cerebral cortex was minced and homogenized (Potter-Elvehjem homogenizer) in 10 volumes of ice-cold sucrose solution. The homogenate was centrifuged (4° C.) at 1000×g for 15 minutes. The resulting supernatant was then centrifuged at 90000×g (30 minutes) and the pellet was washed twice with 20 ml ice-cold 50 mM Tris-HCl pH 7.4.

The final pellet was resuspended in 50 mM Tris-HCl pH 7.4/150 mM NaCl/1 mM CaCl$_2$ to give a protein concentration of 4 mg/ml.

The membrane suspension was kept on ice until used. Binding assays were performed in subdued light to prevent dihydropyridine breakdown. Membrane protein (400 µg/tube) was incubated in 50 mM Tris-HCl buffer (pH 7.4)/150 mM NaCl/1 mM CaCl$_2$ with the indicated concentrations of radioligand and test compounds or known calcium antagonists, in a total volume of 2 ml. After the indicated time intervals, the reaction was terminated by rapid filtration through Whatman GF/B glass fiber filters (2.4 cm diameter) on a Millipore filter holder. The assay tube was rinsed with 2 ml ice-cold 50 mM Tris-HCl pH (7.4) and the precipitate was further washed with 2×5 ml of the same buffer.

Filters were dried under a heat lamp and were extracted with 10 ml of liquid scintillation cocktail (Toluene/Triton X-100, 2/1 containing 4 g Omnifluor/1) prior to tritium determination at 48% counting efficiency.

Non specific binding was determined in presence of 1.0 µM unlabeled Nifedipine and was subtracted from the total binding to yield what will be called "specific binding". Assays were performed in duplicate or triplicate.

Data were expressed as percent specific [$^3$H]-Nitrendipine binding relative to the established control value.

Compound activity in the [$^3$H]-Nitrendipine binding assay was evaluated by using the following criteria:

1. [$^3$H]-Nitrendipine binding at 1.0 µM compound final concentration was either below 95% or above 105% of the control value determined in absence of compound.
2. The ratio obtained by dividing the amount of specifically found [$^3$H]-Nitrendipine at 1.0 µM compound final concentration by the value obtained at 0.1 µM test compound, was smaller than 0.9 or greater than 1.1. This ratio is indicative of a dose response relationship within the compound concentration range tested, when the value differs appreciably from 1.0.

Note: In some experiments [$^3$H]-PN200 110, a new and commercially available specific dihydropyridine was used instead of [$^3$H]-Nitrendipine. Results were comparable to those obtained with [$^3$H]-Nitrendipine.

(c) Results

The amount of specifically bound [$^3$H]-Nitrendipine was measured in the presence of 1 µM of known calcium antagonists used as reference standards.

The following results expressed as % [$^3$H]-Nitrendipine bound were obtained: TMB-8 (95%), Flunarizine (55%), Prenylamine (57%), Verapamil (44%) and Nifedipine (0%).

It can clearly be seen (in table 1a) that among the selected 1,3-diphosphonates tested there are strong inhibitors (compounds 38, 79, 66, 88, 68, 113, 117, 83, 73, 75) and activators (compounds 55 and 56) of [$^3$H]-Nitrendipine binding. When the more specific dihydropyridine [$^3$H]-PN200 110 was used (table 1b) similar results were obtained with compound 79 used as internal standard and several compounds as potent as Nifedipine were discovered: such as compounds 90, 93, 92, 89 and 106. It should be noted that many 1,3-diphosphonates are more active than the reference calcium antagonists listed above.

These results are the direct proof of the interaction of 1,3-diphosphonates with the calcium channel and/or its regulatory sites. To our knowledge this is the first discovery of a class of compounds which display the complete spectrum of [$^3$H]-Nitrendipine binding modulation. Until now inhibition and stimulation of [$^3$H]-Nitrendipine binding have been displayed by compounds differing widely in their chemical structures (Verapamil and Diltiazem).

TABLE 1a
EFFECT OF 1,3-DIPHOSPHONATES ON [$^3$H]—NITRENDIPINE BINDING TO RAT BRAIN MEMBRANES

| Compound | Specifically bound[$^3$H]—Nitrendipine % of control value compound concentration-1.0 μM | Bound $^3$H at 1.0 μM Bound $^3$H at 0.1 μM |
|---|---|---|
| 2 | 98 | 1.002 |
| 3 | 94 | 0.955 |
| 4 | 99 | 0.957 |
| 5 | 99 | 1.003 |
| 10 | 92 | 0.983 |
| 11 | 96 | 1.024 |
| 25 | 100 | 1.060 |
| 40 | 100 | 0.978 |
| 26 | 89 | 1.018 |
| 27 | 95 | 0.982 |
| 30 | 99 | 1.003 |
| 36 | 100 | 0.966 |
| 37 | 104 | 1.011 |
| 38 | 60 | 0.721 |
| 39 | 110 | 1.220 |
| 55 | 156 | 1.292 |
| 56 | 115 | 1.115 |
| 73 | 81 | 0.862 |
| 74 | 17 | 0.380 |
| 75 | 22 | 0.354 |
| 111 | 57 | 0.809 |
| 79 | 0 | 0.000 |
| 83 | 36 | 0.548 |
| 82 | 90 | 0.886 |
| 84 | 80 | 0.886 |
| 86 | 98 | 1.052 |
| 85 | 112 | 1.082 |
| 87 | 93 | 0.967 |
| 66 | 26 | 0.387 |
| 88 | 69 | 0.760 |
| 68 | 0 | 0.000 |
| 112 | 0 | 0.645 |
| 113 | 20 | 0.621 |
| 117 | 79 | 0.950 |

TABLE 1b
EFFECT OF 1,3-DIPHOSPHONATES ON [$^3$H]—PN-200 110 BINDING TO RAT BRAIN MEMBRANES

| Compound Number | Specificallly bound[$^3$H]—PN-200 110 % of control value compound concentration-1.0 μM | Bound $^3$H at 1.0 μM Bound $^3$H at 0.1 μM |
|---|---|---|
| 52 | 9 | 0.227 |
| 79 | 3 | 0.211 |
| 110 | 13 | 0.294 |
| 98 | 19 | 0.780 |
| 99 | 56 | 0.627 |
| 90 | 4 | 0.243 |
| 77 | 19 | 0.337 |
| 101 | 47 | 0.527 |
| 102 | 89 | 0.925 |
| 100 | 38 | 0.504 |
| 93 | 0 | 0.000 |
| 92 | 0 | 0.000 |
| 89 | 6 | 0.310 |
| 91 | 15 | 0.420 |
| 106 | 42 | 0.570 |
| 104 | 59 | 0.687 |

B. INHIBITORY ACTIVITY OF SELECTED 1,3-DIPHOSPHONATES ON RAT TRACHEA CONTRACTION INDUCED BY KCl DEPOLARIZATION (a) Tissue preparation Spontaneously hypertensive male rats (SHR) Okamoto-Aoki Strain, weighing 300–400 g were used in this study. They were killed by bleeding after Pentobarbital anesthesia (Nembutal, Abbott Co, 40 mg/kg). Their entire trachea was quickly removed and dissected free of fat and connective tissue in Krebs-Ringer solution. A strip (4 mm×40 mm), obtained by spirally cutting the trachea, was immediately suspended in a 50 ml Krebs-Ringer solution and continuously bubbled with a O$_2$/CO$_2$ (95/5) mixture. Bath temperature was maintained at 37±1° C. The composition (mM) of the Krebs-Ringer solution modified by Nghiem, was as follows: NaCl, (118.0); KCl, (4.7); CaCl$_2$, (2.5); MgCl$_2$, (1.18); NaHCO$_3$, (12.5); KH$_2$PO$_4$, (1.18); glucose, (5.5) in bidistilled water (pH 7.4). Each strip was equilibrated under initial tension (1.5–2 g) for 1–2 hours and the bath solution changed every 30 min. A contractile or relaxant response was isometrically measured with a force-displacement transducer (Ugo-Basile) and recorded on a polygraph (Beckman).

(b) Relaxant activity of 1,3-diphosphonates

After equilibration, KCl was added to the bath at 65 mM final concentration. This concentration produced maximum trachea contraction. Under these conditions, a plateau phase showing a tonic sustained contraction was reached within 30 minutes. Drugs were added 30 minutes after the plateau phase has been reached (final concentration=1.0 μM). The volume of added drug solutions did not exceed 100 μl. Recordings of the residual trachea contraction were made 40 minutes after drug addition to the bathing fluid. The initial KCl induced contraction was taken as the maximum KCl response (100%). Results were expressed as % of maximal contraction. Nifedipine, Prenylamine, Flunarizine and Diltiazem were used as reference standards to validate this assay.

(c) Compounds and Drugs

All 1,3-diphosphonates and drugs were dissolved in saline (0.9% NaCl) except when water insoluble, then the compounds were dissolved in 2% ethanol. The final concentration of ethanol used has been shown not to interfere with the assay.

(d) Statistical Analysis

Results are expressed as mean values±SEM, the Student's t-test was used for statistical analysis. Compounds which decrease the maximal KCl contraction (100%) to at least 95% are considered as demonstrating activity.

(e) Results

In this screening model compounds 25, 37, 55, 73, 40, 74, 75, 79, 83, 38, 87, 88, 117 were found to display a potent pharmacological activity. These results confirm the potential use of 1,3-diphosphonates as smooth muscle relaxant drugs for example in the treatment of asthma.

TABLE 2

INHIBITORY ACTIVITY OF 1,3-DIPHOSPHONATES ON KCL-INDUCED RAT TRACHEA CONTRACTION

| Compound Number | Contraction (% max.) |
|---|---|
| 10 | 91.0 ± 0.0 |
| 25 | 53.0 ± 2.5 |
| 30 | 90.0 ± 0.0 |
| 37 | 53.8 ± 0.4 |
| 38 | 84.0 ± 2.4 |
| 40 | 61.2 ± 4.6 |
| 39 | 96.0 ± 4.9 |
| 55 | 73.0 ± 1.0 |
| 56 | 100.0 ± 0.0 |
| 73 | 46.2 ± 1.8 |
| 74 | 35.0 ± 1.2 |
| 75 | 70.0 ± 3.0 |
| 111 | 100.1 ± 1.5 |
| 79 | 60.3 ± 9.6 |
| 83 | 62.5 ± 11.5 |
| 82 | 80.0 ± 4.0 |
| 84 | 98.5 ± 2.5 |
| 86 | 89.0 ± 2.0 |
| 85 | 96.2 ± 0.8 |
| 87 | 71.9 ± 1.9 |
| 66 | 88.5 ± 0.5 |
| 88 | 56.3 ± 5.9 |
| 68 | 100.0 ± 4.0 |
| 112 | 84.0 ± 3.0 |
| 113 | 90.0 ± 1.5 |
| 117 | 60.0 ± 4.0 |

C. EFFECT OF SELECTED 1,3-DIPHOSPHONATES ON ISOLATED RAT ATRIUM RATE

(a) Methods

Spontaneously hypertensive male rats (SHR) (Okamoto-Aoki strain) were anesthetized with Pentobarbital (Nembutal Abbott, 60 mg/kg, i.p.). The hearts were quickly excised and both atria were dissected free from adjacent cardiac tissues. The atria were immediatly placed in a 50 ml Krebs-Ringer bath with the following composition (mM): NaCl, (120.0); KCl, (5.63); $CaCl_2$, (2.0); $MgCl_2$, (2.10); $NaHCO_3$, (25.0); Glucose, (9.7) (pH 7.4). The solution was continuously bubbled with a $O_2/CO_2$ mixture (95/5) and maintained at 37±1° C. The atrium was fixed to an optical displacement transducer (IITC, USA) under a resting tension of 1 g in order to measure atrial rate. The preparation was allowed to equilibrate for 40 min then cumulative dose-response curves were determined for each test compound (0.5–5 μMole/l). Maximum effect was normally obtained within 30–40 min. for each concentration.

(b) Compounds

Stock solutions of the 1,3-diphosphonates were generally prepared in 0.9% saline and water insoluble compounds were prepared in 50% ethanol. The final ethanol concentration was found to have no detectable effect on atrium rate. When tested at the concentration of $5.0 \times 10^{-6}$M a decrease in atrium rate of more than 5% was considered as significant.

Results

All data are presented as % decrease of initial atrium rate (mean values±SEM). A potent negative chronotropic effect was found with all compounds tested (table 3). The potential use of 1,3-diphosphonates in cardiac diseases and arrhythmias is illustrated by activity displayed in this assay.

TABLE 3

CHRONOTROPIC ACTIVITY OF 1,3-DIPHOSPHONATES IN RAT ATRIUM

| Compound | Decrease in atrium rate (% pretest) $5.0 \times 10^{-6}$ M |
|---|---|
| 55 | 17.5 ± 4.6 |
| 73 | 18.8 ± 11.2 |
| 74 | 8.3 ± 4.5 |
| 75 | 14.8 ± 4.8 |
| 83 | 4.4 ± 0.6 |

D. HYPOTENSIVE ACTIVITY OF 1,3-DIPHOSPHONATES IN RAT

* Intravenous hypotensive activity

(a) Methods

Male Wistar rats were anesthetized with Pentobarbital (Nembutal, 60 mg/kg i.p.) and heparinized (5 mg/kg i.p.). After tracheotomy the right carotid was cannulated (catheter PE 50); blood pressure was measured with a pressure transducer (Statham P 23 db) and recorded on a polygraph (Beckman).

(b) Compounds and Drugs

Animals received 0.5 and 1.5 mg/kg of the test compounds. Less than 100 μl of test compounds dissolved in 0.9% saline were injected in the jugular vein. Highly water insoluble compounds were suspended in 2% Tween-80. Injection of the vehicle alone had no detectable hypotensive effect.

(c) Results

Results presented are expressed as percent decrease in initial mean blood pressure (Mean±SEM). A definite hypotensive activity was displayed acutely by all the 1,3-diphosphonates tested. It should also be noted that 1,3-diphosphonates such as compounds 73, 74 and 82, demonstrate hypotensive activity superior to that of classical hypotensive drugs and of the calcium antagonists used as references (table 4).

TABLE 4
ACUTE I.V. HYPOTENSIVE ACTIVITY OF 1,3-DIPHOSPHONATES AND KNOWN HYPOTENSIVE DRUGS IN RAT

| Compound Number | Decrease in mean blood pressure (% pretest) | |
|---|---|---|
| | 0.5 mg/kg | 1.5 mg/kg |
| 25 | 23.2 ± 2.2 | 41.4 ± 1.0 |
| 26 | 18.1 ± 3.0 | 41.6 ± 1.3 |
| 27 | 25.6 ± 2.2 | 35.0 ± 4.7 |
| 30 | 17.0 ± 0.0 | 34.4 ± 5.1 |
| 36 | 39.9 ± 1.6 | |
| 33 | 13.2 ± 0.0 | 16.0 ± 0.6 |
| 55 | 28.2 ± 0.7 | 31.1 ± 6.4 |
| 73 | 50.0 ± 3.8 | |
| 74 | 50.8 ± 2.7 | |
| 75 | 22.8 ± 1.6 | |
| 83 | 10.6 ± 0.5 | |
| 82 | 40.1 ± 3.2 | |

| Drugs | Decrease in mean blood pressure (% pretest) 1.0 mg/kg |
|---|---|
| Captopril | 0 |
| Propranolol | 11.8 ± 1.1 |
| Methyl Dopa | 0 |
| Diltiazem | 47.9 ± 0.0 |

\* Oral hypotensive activity in hypertensive rats

Since calcium antagonists have been shown to be hypotensive drugs, the spontaneously hypertensive rat (SHR) was used as an additional animal model to demonstrate the oral hypotensive activity of 1,3-diphosphonates. Some selected compounds were given orally to conscious SHR rats and blood pressure was monitored using the tail cuff method. A marked and sustained hypotensive activity was measured in all treated rats. Results are given 2 hours post dose (Table 5). These studies illustrate the obvious potential use of orally administered 1,3-diphosphonates for the clinical treatment of hypertension in man. Several compounds: 79, 90, 93, 92, 89 and 91 were found to decrease blood pressure as markedly as the marketed calcium antagonists used as references for which clinical use as antihypertensive agents have been approved.

TABLE 5
EFFECT OF SELECTED 1,3-DIPHOSPHONATES AND REFERENCE COMPOUNDS ON BLOOD PRESSURE IN HYPERTENSIVE RATS

| Compound Number | Decrease in blood pressure (% pretest value) |
|---|---|
| 83 | 15 |
| 74 | 12 |
| 75 | 37–41 |
| 79 | 37–50 |
| 50 | 8 |
| 56 | 3 |
| 52 | 17 |
| 112 | 18 |
| 113 | 19 |
| 110 | 44 |
| 82 | 11 |
| 66 | 23 |
| 80 | 32 |
| 98 | 38 |
| 90 | 55 |
| 44 | 14 |
| 93 | 62 |
| 92 | 48 |
| 89 | 44 |
| 91 | 49 |
| 104 | 10 |
| Diltiazem | 38 |
| Verapamil | 57 |
| Nifedipine | 47 |
| Flunarizine | 23 |

PREFERRED MODE OF ADMINISTRATION

The 1,3-diphosphonates can be administered preferably in the form of capsules, tablets or granules, which can be accomplished by mixing the active principle, a pharmaceutical carrier and various ingredients currently used for pharmaceutical preparation.

As used herein, the term "pharmaceutical carrier" denotes a solid or liquid filler diluent or encapsulating substance. Some examples of the substances which can serve as pharmaceutical carriers are sugars such as lactose, glucose and sucrose; starches such as corn starch and potato starch; cellulose and its derivatives, such as sodium carboxymethylcellulose, ethylcellulose, cellulose acetate; powdered tragacanth; malt; gelatin; talc; stearic acid; magnesium stearate; calcium sulfate; vegetable oils, such as peanut oil, cottonseed oil, sesame oil, olive oil, corn oil and oil of theobroma; polyols such as propylene glycol, glycerin, sorbitol, mannitol, and polyethylene glycol; agar; alginic acid; pyrogen-free water; isotonic saline and phosphate buffer solutions, as well as other non-toxic compatible substances used in pharmaceutical formulations. Wetting agents and lubricants such as sodium lauryl sulfate, as well as coloring agents, flavoring agents and preservatives, can also be present. Tableting is done using conventional techniques.

The pharmaceutical carrier employed in conjunction with the phosphonates is used at a concentration sufficient to provide a practical size to dosage relationship. Preferably the pharmaceutical carrier comprises from about 0.1% to 99% by weight of the total composition.

Example 1

Gelatin capsules are prepared by conventional methods comprising:

| INGREDIENTS | mg/CAPSULE |
|---|---|
| compound 79 | 300 |
| Gelatin | 100 |
| Glycerine | 50 |
| Potassium Sorbate | 0.5 |

Example 2

Tablets are prepared by conventional methods using preferably 1,3-diphosphonates in their cristalline form:

| INGREDIENTS | mg/TABLET |
|---|---|
| Compound 102 | 100 |
| Hydroxy Propyl Methyl Cellulose | 50 |
| Magnesium Stearate | 3 |

For direct inhalation therapy, an aerosol spray delivering 0.1 to 10 mg/kg per day of a pharmaceutically acceptable 1,3-diphosphonate can be used.

For the treatment of specific diseased states, composition containing a pharmaceutically acceptable 1,3-diphosphonate can be administered as a solution, suspension, emulsion or by simultaneous, intradermal, intramuscular, intravenous or intraperitoneal injection.

Rectal administration of 1,3-diphosphonates can be performed by incorporating the active principle into conventional jelly bases: glycerin, "Imhausen" etc. to produce suppositories.

We claim:

1. 1,3-propylidenediphosphonate derivatives of the formula

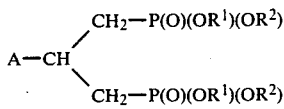

wherein $R^1$ and $R^2$ are each selected from the group consisting of hydrogen, sodium potassium, magnesium, ammonium, and $C_{1-8}$ alkyl; and A is selected from the group consisting of

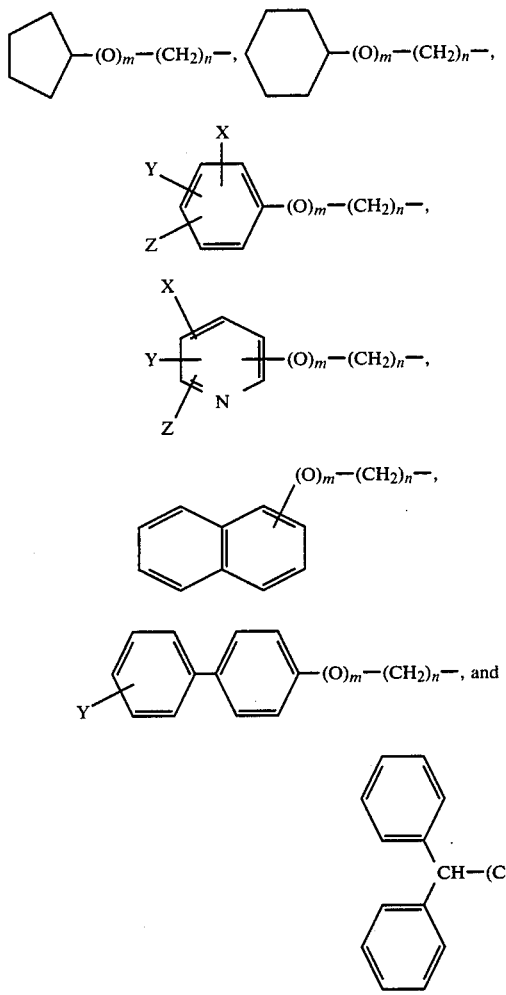

wherein m is zero or 1, n is an integer from zero to 8, and X, Y and Z are each selected from the group consisting of H, F, Cl, Br, I, $CF_3$, $CHF_2$, $NO_2$, CN, $CH_3$, $C_2H_5$, $CH=CH-CH_2$, n-propyl, isopropyl, n-butyl, isobutyl, t-butyl, OH, $CH_2OH$, $-OCH_2O-$, $OCH_3$, $OC_2H_5$, $OC_3H_7$, $OC_4H_9$, $SCH_3$, $NH_2$, $NMe_2$, $NEt_2$, $(CH_2)_t-NMe_2$, and $(CH_2)_t-NEt_2$ wherein t is an integer from 1 to 4.

2. 2-(2-phenoxyethyl)-1,3-propylidenediphosphonic acid according to claim 1.
3. Tetramethyl 2-(2-phenoxyethyl)-1,3-propylidenediphosphonate according to claim 1.
4. Tetraethyl 2-(2-phenoxyethyl)-1,3-propylidenediphosphonate according to claim 1.
5. Tetraethyl 2-(1, naphthylmethyl)-1,3-propylidenediphosphonate according to claim 1.
6. Tetraethyl 2-(4-biphenylmethyl)-1,3-propylidenediphosphonate according to claim 1.
7. Tetrapropyl 2-(2-phenoxyethyl)-1,3-propylidenediphosphonate according to claim 1.
8. Tetraisopropyl 2-benzyl-1,3-propylidenediphosphonate according to claim 1.
9. Tetraisopropyl 2-(2-phenoxyethyl)-1,3-propylidenediphosphonate according to claim 1.
10. Tetrabutyl 2-(2-phenylethyl)-1,3-propylidenediphosphonate according to claim 1.
11. Tetrabutyl 2-(3-phenylpropyl)-1,3-propylidenediphosphonate according to claim 1.
12. Tetrabutyl 2-(2-phenoxyethyl)-1,3-propylidenediphosphonate according to claim 1.
13. Tetrabutyl 2-(3-phenoxypropyl)-1,3-propylidenediphosphonate according to claim 1.
14. Tetrabutyl 2-[3-(3-pyridyl)propyl]-1,3-propylidenediphosphonate according to claim 1.
15. Tetrabutyl 2-[2-(4-fluorophenoxy)ethyl]-1,3-propylidenediphosphonate according to claim 1.
16. Tetrabutyl 2-[2-(3-trifluoromethylphenoxy)ethyl]-1,3-propylidenediphosphonate according to claim 1.
17. Tetraisobutyl 2-(3-phenylpropyl)-1,3-propylidenediphosphonate according to claim 1.
18. Tetrapentyl 2-(3-phenylpropyl)-1,3-propylidenediphosphonate according to claim 1.
19. Tetrahexyl 2-(3-phenylpropyl)-1,3-propylidenediphosphonate according to claim 1.
20. Bis(ethyl, pentyl) 2-(3-phenylpropyl)-1,3-propylidenediphosphonate according to claim 1.
21. Bis(butyl, ethyl) 2-(3-phenylpropyl)-1,3-propylidenediphosphonate according to claim 1.
22. Bis(methyl, hydrogen) 2-benzyl-1,3-propylidenediphosphonate according to claim 1.
23. A method for treating hypertension, comprising administering orally or intravenously to a human in need of a said treatment an anti-hypertensively effective amount of a compound according to claim 1.
24. Method according to claim 23 in which the compound is tetrabutyl 2-(3-phenylpropyl)-1,3-propylidenediphosphonate.
25. Method according to claim 23 in which the compound is tetrabutyl 2-(2-phenoxyethyl)-1,3-propylidenediphosphonate.
26. Method according to claim 23 in which the compound is tetrabutyl 2-(3-phenoxypropyl)-1,3-propylidenediphosphonate.
27. Method according to claim 23 in which the compound is tetrabutyl 2-[2-(4-fluorophenoxy)ethyl]-1,3-propylidenediphosphonate.
28. Method according to claim 23 in which the compound is tetrabutyl 2-[2-(3-trifluoromethylphenoxy)ethyl]-1,3-propylidenediphosphonate.
29. An anti-hypertensive composition comprising an anti-hypertensively effective amount of a compound according to claim 1 in combination with a pharmaceutically acceptable excipient.

* * * * *